US012098425B2

(12) United States Patent
Daugharthy et al.

(10) Patent No.: US 12,098,425 B2
(45) Date of Patent: Sep. 24, 2024

(54) THREE-DIMENSIONAL SPATIAL MOLECULAR INDEXING

(71) Applicant: ReadCoor, LLC, Pleasanton, CA (US)

(72) Inventors: Evan Daugharthy, Cambridge, MA (US); Richard Terry, Carlisle, MA (US)

(73) Assignee: READCOOR, LLC, Pleasanton, CA (US)

( * ) Notice: Subject to any disclaimer, the term of this patent is extended or adjusted under 35 U.S.C. 154(b) by 785 days.

(21) Appl. No.: 17/225,659

(22) Filed: Apr. 8, 2021

(65) Prior Publication Data

US 2021/0292834 A1 Sep. 23, 2021

Related U.S. Application Data

(63) Continuation of application No. PCT/US2019/055434, filed on Oct. 9, 2019.

(60) Provisional application No. 62/853,876, filed on May 29, 2019, provisional application No. 62/743,836, filed on Oct. 10, 2018.

(51) Int. Cl.
*C12Q 1/68* (2018.01)
*C12Q 1/6806* (2018.01)
*C12Q 1/6874* (2018.01)
*C12Q 1/6844* (2018.01)

(52) U.S. Cl.
CPC ......... *C12Q 1/6874* (2013.01); *C12Q 1/6806* (2013.01); *C12Q 1/6844* (2013.01)

(58) Field of Classification Search
CPC .................................................. C12Q 1/6869
See application file for complete search history.

(56) References Cited

U.S. PATENT DOCUMENTS

| | | |
|---|---|---|
| 3,501,459 A | 3/1970 | Schindler et al. |
| 3,551,710 A | 12/1970 | Gourdine |
| 3,871,445 A | 3/1975 | Wanka et al. |
| 3,993,233 A | 11/1976 | Bartell |
| 4,123,610 A | 10/1978 | Summerton et al. |
| 4,844,617 A | 7/1989 | Kelderman et al. |
| 4,886,741 A | 12/1989 | Schwartz |
| 4,981,985 A | 1/1991 | Kaplan et al. |
| 5,116,742 A | 5/1992 | Cech et al. |
| 5,151,189 A | 9/1992 | Hu et al. |
| 5,244,797 A | 9/1993 | Kotewicz et al. |
| 5,424,413 A | 6/1995 | Hogan et al. |
| 5,563,056 A | 10/1996 | Swan et al. |
| 5,594,235 A | 1/1997 | Lee |
| 5,635,352 A | 6/1997 | Urdea et al. |
| 5,684,149 A | 11/1997 | Morrow |
| 5,695,940 A | 12/1997 | Drmanac et al. |
| 5,795,236 A | 8/1998 | Alberts et al. |
| 5,830,708 A | 11/1998 | Naughton |
| 5,834,758 A | 11/1998 | Trulson et al. |
| 5,871,921 A | 2/1999 | Landegren et al. |
| 6,063,612 A | 5/2000 | Jayasena et al. |
| 6,068,979 A | 5/2000 | Akhavan-Tafti |
| 6,083,726 A | 7/2000 | Mills, Jr. et al. |
| 6,194,148 B1 | 2/2001 | Hori et al. |
| 6,221,603 B1 | 4/2001 | Mahtani |
| 6,232,067 B1 | 5/2001 | Hunkapiller et al. |
| 6,306,597 B1 | 10/2001 | Macevicz |
| 6,534,266 B1 | 3/2003 | Singer |
| 6,586,176 B1 | 7/2003 | Trnovsky et al. |
| 6,632,655 B1 | 10/2003 | Mehta et al. |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,745,129 B1 | 6/2010 | Schatz |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Bálint, et al. Correlative live-cell and superresolution microscopy reveals cargo transport dynamics at microtubule intersections. Proceedings of the National Academy of Sciences. Feb. 26, 2013;110(9): pp. 3375-3380.

Chen et al. "Spatially resolved, highly multiplexed RNA profiling in single cells". Science. Apr. 24, 2015;348(6233):aaa6090, pp. 1-14.

Kleinstiver, BP et al. "High-Fidelity CRISPR-Cas9 Variants With Undetectable Genome-Wide Off-Targets," Nature, Jan. 28. 2016, vol. 529, No. 7587, 490-495; abstract. DOI: 10.1038/nature16526.

(Continued)

*Primary Examiner* — Kenneth R Horlick
(74) *Attorney, Agent, or Firm* — Wilson Sonsini Goodrich & Rosati

(57) ABSTRACT

The present disclosure provides methods and systems for generating and using indices in a synthetic three-dimensional (3D) matrix within a biological sample (e.g., a cell or a tissue sample). The present disclosure provides a method for processing or analyzing a nucleic acid molecule having a three-dimensional (3D) spatial position in a cell or cell derivative can comprise: (a) using a transposase to insert a nucleic acid index sequence into the nucleic acid molecule to generate an indexed nucleic acid molecule comprising the nucleic acid index sequence; (b) detecting the nucleic acid index sequence of the indexed nucleic acid molecule to identify the 3D spatial position; (c) subsequent to (b), removing the indexed nucleic acid molecule or derivative thereof from the 3D spatial position; and (d) identifying a sequence of the indexed nucleic acid molecule or derivative thereof removed from the 3D spatial position in (c).

20 Claims, 4 Drawing Sheets

(56) References Cited

U.S. PATENT DOCUMENTS

| | | |
|---|---|---|
| 7,771,949 B2 | 8/2010 | Kramer |
| 7,906,285 B2 | 3/2011 | Drmanac |
| 7,910,304 B2 | 3/2011 | Drmanac |
| 7,941,279 B2 | 5/2011 | Hwang et al. |
| 7,989,166 B2 | 8/2011 | Koch et al. |
| 8,013,134 B2 | 9/2011 | Fredriksson |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,329,404 B2 | 12/2012 | McKernan et al. |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,946,389 B2 | 2/2015 | Gao et al. |
| 8,986,926 B2 | 3/2015 | Ferree et al. |
| 8,993,233 B2 | 3/2015 | Zhang et al. |
| 8,999,641 B2 | 4/2015 | Zhang et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,232,067 B2 | 1/2016 | Leigh et al. |
| 9,257,135 B2 | 2/2016 | Ong et al. |
| 9,267,135 B2 | 2/2016 | Church et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,896,720 B2 | 2/2018 | Raj et al. |
| 9,909,167 B2 | 3/2018 | Samusik et al. |
| 9,914,967 B2 | 3/2018 | Church et al. |
| 10,030,261 B2 | 7/2018 | Frisen et al. |
| 10,032,064 B2 | 7/2018 | Hoyt |
| 10,036,055 B2 | 7/2018 | Church et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,664 B2 | 12/2019 | Doudna et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,538,795 B2 | 1/2020 | Seitz et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,858,692 B2 | 12/2020 | Church et al. |
| 10,872,679 B2 | 12/2020 | Cai et al. |
| 10,964,001 B2 | 3/2021 | Miller |
| 11,021,737 B2 | 6/2021 | Church et al. |
| 11,021,741 B2 | 6/2021 | Wu et al. |
| 11,078,520 B2 | 8/2021 | Church et al. |
| 11,085,072 B2 | 8/2021 | Church et al. |
| 11,111,521 B2 | 9/2021 | Church et al. |
| 11,118,220 B2 | 9/2021 | Daugharthy et al. |
| 11,193,163 B2 | 12/2021 | Daugharthy et al. |
| 11,293,051 B2 | 4/2022 | Church et al. |
| 11,293,052 B2 | 4/2022 | Church et al. |
| 11,293,054 B2 | 4/2022 | Levner et al. |
| 11,299,767 B2 | 4/2022 | Church et al. |
| 11,312,992 B2 | 4/2022 | Church et al. |
| 11,447,807 B2 | 9/2022 | Church et al. |
| 11,473,139 B2 | 10/2022 | Church et al. |
| 11,542,554 B2 | 1/2023 | Daugharthy et al. |
| 11,549,136 B2 | 1/2023 | Church et al. |
| 11,566,276 B2 | 1/2023 | Church et al. |
| 11,566,277 B2 | 1/2023 | Church et al. |
| 11,639,518 B2 | 5/2023 | Church et al. |
| 11,713,485 B2 | 8/2023 | Daugharthy et al. |
| 11,718,874 B2 | 8/2023 | Daugharthy et al. |
| 2001/0039018 A1 | 11/2001 | Matson et al. |
| 2002/0015952 A1 | 2/2002 | Anderson et al. |
| 2002/0029979 A1 | 3/2002 | Freund et al. |
| 2002/0049176 A1 | 4/2002 | Anderson et al. |
| 2002/0155989 A1 | 10/2002 | Efimov et al. |
| 2002/0168645 A1 | 11/2002 | Taylor |
| 2002/0172950 A1 | 11/2002 | Kenny et al. |
| 2003/0018984 A1 | 1/2003 | Coleman et al. |
| 2003/0148335 A1 | 8/2003 | Shen et al. |
| 2003/0165852 A1 | 9/2003 | Schueler et al. |
| 2004/0006035 A1 | 1/2004 | Macejak et al. |
| 2004/0077014 A1 | 4/2004 | Becker |
| 2004/0081962 A1 | 4/2004 | Chen et al. |
| 2004/0081979 A1 | 4/2004 | Knezevic et al. |
| 2004/0126770 A1 | 7/2004 | Kumar et al. |
| 2004/0152072 A1 | 8/2004 | Gerard |
| 2004/0248144 A1 | 12/2004 | Mir |
| 2004/0259190 A1 | 12/2004 | Naughton |
| 2004/0259226 A1 | 12/2004 | Robey et al. |
| 2005/0032694 A1 | 2/2005 | Sonderegger |
| 2005/0064435 A1 | 3/2005 | Su et al. |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0221304 A1 | 10/2005 | Xiang et al. |
| 2005/0233318 A1 | 10/2005 | Chee et al. |
| 2006/0024711 A1 | 2/2006 | Lapidus et al. |
| 2006/0046311 A1 | 3/2006 | Sun et al. |
| 2006/0077536 A1 | 4/2006 | Bromage et al. |
| 2006/0088868 A1 | 4/2006 | Evans et al. |
| 2006/0127916 A1 | 6/2006 | Seul et al. |
| 2006/0177833 A1 | 8/2006 | Brenner |
| 2006/0183107 A1 | 8/2006 | Melkonyan |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0003949 A1 | 1/2007 | Rava |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0172873 A1 | 7/2007 | Brenner et al. |
| 2007/0190543 A1 | 8/2007 | Livak |

(56) References Cited

U.S. PATENT DOCUMENTS

| | | |
|---|---|---|
| 2007/0206275 A1 | 9/2007 | Hemmer et al. |
| 2007/0212700 A1 | 9/2007 | Ranganathan et al. |
| 2007/0231823 A1 | 10/2007 | McKernan et al. |
| 2007/0292877 A1 | 12/2007 | Dimitrov |
| 2008/0003586 A1 | 1/2008 | Hyde et al. |
| 2008/0003599 A1 | 1/2008 | Dary et al. |
| 2008/0050718 A1 | 2/2008 | Gesteland et al. |
| 2008/0176769 A1 | 7/2008 | Rank et al. |
| 2008/0180790 A1 | 7/2008 | Tafas et al. |
| 2008/0269068 A1 | 10/2008 | Church et al. |
| 2009/0105082 A1 | 4/2009 | Chetverin et al. |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2009/0269739 A1 | 10/2009 | Cech et al. |
| 2009/0280559 A1 | 11/2009 | McCarthy |
| 2010/0009868 A1 | 1/2010 | Yan et al. |
| 2010/0015607 A1 | 1/2010 | Geiss et al. |
| 2010/0049448 A1 | 2/2010 | Doyle et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0090562 A1 | 4/2011 | Brooker |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0208040 A1 | 8/2011 | Carmi et al. |
| 2011/0216953 A1 | 9/2011 | Callahan et al. |
| 2011/0223585 A1 | 9/2011 | Gullberg et al. |
| 2011/0223638 A1 | 9/2011 | Wiedenheft et al. |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0065091 A1 | 3/2012 | Willis et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0308695 A1 | 10/2014 | Bruce et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0031089 A1 | 1/2015 | Lindstrom |
| 2015/0050653 A1 | 2/2015 | Fekete et al. |
| 2015/0098126 A1 | 4/2015 | Keller et al. |
| 2015/0133319 A1 | 5/2015 | Fu et al. |
| 2015/0225773 A1 | 8/2015 | Farmer et al. |
| 2015/0247150 A1 | 9/2015 | Zhang et al. |
| 2015/0267251 A1 | 9/2015 | Cai et al. |
| 2016/0002704 A1 | 1/2016 | Diehl et al. |
| 2016/0024524 A1 | 1/2016 | Joung et al. |
| 2016/0053304 A1 | 2/2016 | Wurtzel et al. |
| 2016/0106439 A1 | 4/2016 | Menashe |
| 2016/0108458 A1 | 4/2016 | Frei et al. |
| 2016/0153006 A1 | 6/2016 | Zhang et al. |
| 2016/0160210 A1 | 6/2016 | Mali et al. |
| 2016/0265046 A1 | 9/2016 | Zhang et al. |
| 2016/0289740 A1 | 10/2016 | Fu et al. |
| 2016/0305856 A1 | 10/2016 | Boyden et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2016/0369321 A1 | 12/2016 | Landegren et al. |
| 2016/0376642 A1 | 12/2016 | Landegren et al. |
| 2017/0009278 A1 | 1/2017 | Söderberg et al. |
| 2017/0010672 A1 | 1/2017 | Tanaka et al. |
| 2017/0081489 A1 | 3/2017 | Rodriques et al. |
| 2017/0176338 A1 | 6/2017 | Wu et al. |
| 2017/0191078 A1 | 7/2017 | Zhang et al. |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1 | 1/2018 | Pierce et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0282787 A1 | 10/2018 | Walter et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0085383 A1 | 3/2019 | Church et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0194709 A1 | 6/2019 | Church et al. |
| 2019/0218608 A1 | 7/2019 | Daugharthy et al. |
| 2019/0241938 A1 | 8/2019 | Levner et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0330617 A1 | 10/2019 | Church et al. |
| 2020/0009786 A1 | 1/2020 | Hikmet et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0087611 A1 | 3/2021 | Church et al. |
| 2021/0102244 A1 | 4/2021 | Church et al. |
| 2021/0115504 A1 | 4/2021 | Cai et al. |
| 2021/0277389 A1 | 9/2021 | Church et al. |
| 2021/0310052 A1 | 10/2021 | Daugharthy et al. |
| 2021/0324450 A1 | 10/2021 | Church et al. |
| 2021/0332414 A1 | 10/2021 | Church |
| 2021/0332415 A1 | 10/2021 | Church et al. |
| 2021/0340621 A1 | 11/2021 | Daugharthy et al. |
| 2021/0381049 A1 | 12/2021 | Daugharthy et al. |
| 2022/0016624 A1 | 1/2022 | Daugharthy et al. |
| 2022/0025448 A1 | 1/2022 | Levner et al. |
| 2022/0049303 A1 | 2/2022 | Busby et al. |
| 2022/0145365 A1 | 5/2022 | Church et al. |
| 2022/0228196 A1 | 7/2022 | Church et al. |
| 2022/0251642 A1 | 8/2022 | Church et al. |
| 2022/0282301 A1 | 9/2022 | Levner et al. |
| 2022/0298559 A1 | 9/2022 | Daugharthy et al. |
| 2023/0146821 A1 | 5/2023 | Church et al. |
| 2023/0146985 A1 | 5/2023 | Levner et al. |
| 2023/0212649 A1 | 7/2023 | Church et al. |
| 2023/0227895 A1 | 7/2023 | Church et al. |
| 2023/0279484 A1 | 9/2023 | Daugharthy et al. |
| 2024/0018569 A1 | 1/2024 | Levner et al. |
| 2024/0124932 A1 | 4/2024 | Daugharthy et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |

(56) References Cited

FOREIGN PATENT DOCUMENTS

| | | |
|---|---|---|
| BR | 112015022061 A2 | 11/2017 |
| CA | 2891347 A1 | 6/2014 |
| CN | 1432069 A | 7/2003 |
| CN | 1580283 A | 2/2005 |
| CN | 1959384 A | 5/2007 |
| CN | 101285095 A | 10/2008 |
| CN | 101400803 A | 4/2009 |
| CN | 101553306 A | 10/2009 |
| CN | 101608232 A | 12/2009 |
| CN | 105392898 A | 3/2016 |
| EP | 2288726 A2 | 3/2011 |
| EP | 2465943 A2 | 6/2012 |
| EP | 2798092 A2 | 11/2014 |
| EP | 2878671 A1 | 6/2015 |
| EP | 3425063 A1 | 1/2019 |
| EP | 2794928 B1 | 2/2019 |
| EP | 2971184 B1 | 4/2019 |
| EP | 2766498 B1 | 6/2019 |
| EP | 3578666 A1 | 12/2019 |
| EP | 3847274 A1 | 7/2021 |
| EP | 4108782 B1 | 6/2023 |
| JP | H04268359 A | 9/1992 |
| JP | 2007526772 A | 9/2007 |
| JP | 2009538123 A | 11/2009 |
| JP | 2012170337 A | 9/2012 |
| JP | 2014513523 A | 6/2014 |
| JP | 2015090458 A | 5/2015 |
| KR | 20080003402 A | 1/2008 |
| WO | WO-9746704 A1 | 12/1997 |
| WO | WO-9856955 A1 | 12/1998 |
| WO | WO-9961665 A2 | 12/1999 |
| WO | WO-0126708 A1 | 4/2001 |
| WO | WO-0137266 A1 | 5/2001 |
| WO | WO-03003810 A2 | 1/2003 |
| WO | WO-03044229 A1 | 5/2003 |
| WO | WO-03102233 A1 | 12/2003 |
| WO | WO-2004104645 A2 | 12/2004 |
| WO | WO-2006138257 A2 | 12/2006 |
| WO | WO-2007001986 A2 | 1/2007 |
| WO | WO-2007076128 A2 | 7/2007 |
| WO | WO-2007086900 A2 | 8/2007 |
| WO | WO-2007121489 A2 | 10/2007 |
| WO | WO-2007123744 A2 | 11/2007 |
| WO | WO-2007149696 A1 | 12/2007 |
| WO | WO-2008041104 A2 | 4/2008 |
| WO | WO-2008069973 A2 | 6/2008 |
| WO | WO-2008108989 A2 | 9/2008 |
| WO | WO-2008157696 A2 | 12/2008 |
| WO | WO-2009046149 A1 | 4/2009 |
| WO | WO-2009046348 A1 | 4/2009 |
| WO | WO-2010054108 A2 | 5/2010 |
| WO | WO-2010080134 A1 | 7/2010 |
| WO | WO-2010087325 A1 | 8/2010 |
| WO | WO-2010104533 A2 | 9/2010 |
| WO | WO-2011092596 A2 | 8/2011 |
| WO | WO-2011143124 A2 | 11/2011 |
| WO | WO-2011143583 A1 | 11/2011 |
| WO | WO-2012005595 A2 | 1/2012 |
| WO | WO-2012058638 A2 | 5/2012 |
| WO | WO-2012083189 A2 | 6/2012 |
| WO | WO-2012110899 A2 | 8/2012 |
| WO | WO-2012129242 A2 | 9/2012 |
| WO | WO-2012150035 A1 | 11/2012 |
| WO | WO-2012164565 A1 | 12/2012 |
| WO | WO-2013055995 A2 | 4/2013 |
| WO | WO-2013096851 A1 | 6/2013 |
| WO | WO-2013098244 A1 | 7/2013 |
| WO | WO-2013126794 A1 | 8/2013 |
| WO | WO-2013141680 A1 | 9/2013 |
| WO | WO-2013142578 A1 | 9/2013 |
| WO | WO-2013176772 A1 | 11/2013 |
| WO | WO-2013184754 A2 | 12/2013 |
| WO | WO-2014022702 A2 | 2/2014 |
| WO | WO-2014048083 A1 | 4/2014 |
| WO | WO-2014065596 A1 | 5/2014 |
| WO | WO-2014089290 A1 | 6/2014 |
| WO | WO-2014093595 A1 | 6/2014 |
| WO | WO-2014093622 A2 | 6/2014 |
| WO | WO-2014093661 A2 | 6/2014 |
| WO | WO-2014093694 A1 | 6/2014 |
| WO | WO-2014099744 A1 | 6/2014 |
| WO | WO-2014113493 A1 | 7/2014 |
| WO | WO-2014144288 A1 | 9/2014 |
| WO | WO-2014150624 A1 | 9/2014 |
| WO | WO-2014163886 A1 | 10/2014 |
| WO | WO-2014182528 A2 | 11/2014 |
| WO | WO-2014191518 A1 | 12/2014 |
| WO | WO-2014197568 A2 | 12/2014 |
| WO | WO-2015002813 A1 | 1/2015 |
| WO | WO-2015077318 A1 | 5/2015 |
| WO | WO-2015118029 A1 | 8/2015 |
| WO | WO-2015127183 A2 | 8/2015 |
| WO | WO-2015148606 A2 | 10/2015 |
| WO | WO-2015200378 A1 | 12/2015 |
| WO | WO-2016007839 A1 | 1/2016 |
| WO | WO-2016028887 A1 | 2/2016 |
| WO | WO-2016081740 A1 | 5/2016 |
| WO | WO-2017015018 A1 | 1/2017 |
| WO | WO-2017019456 A2 | 2/2017 |
| WO | WO-2017079382 A1 | 5/2017 |
| WO | WO-2017079406 A1 | 5/2017 |
| WO | WO-2017143155 A2 | 8/2017 |
| WO | WO-2017161251 A1 | 9/2017 |
| WO | WO-2017172860 A1 | 10/2017 |
| WO | WO-2017189525 A1 | 11/2017 |
| WO | WO-2018045181 A1 | 3/2018 |
| WO | WO-2018045186 A1 | 3/2018 |
| WO | WO-2018089445 A1 | 5/2018 |
| WO | WO-2019103996 A1 | 5/2019 |
| WO | WO-2019217758 A1 | 11/2019 |
| WO | WO-2020028194 A1 | 2/2020 |
| WO | WO-2020076976 | 4/2020 |
| WO | WO-2020076979 A1 | 4/2020 |
| WO | WO-2020096687 A1 | 5/2020 |
| WO | WO-2020198071 A1 | 10/2020 |
| WO | WO-2021155063 | 8/2021 |
| WO | WO-2021168326 | 8/2021 |

OTHER PUBLICATIONS

Manders, et al. Direct imaging of DNA in living cells reveals the dynamics of chromosome formation. The Journal of cell biology. Mar. 8, 1999;144(5):813-822.

Tam et al. A Microfluidic Platform for Correlative Live-Cell and Super-Resolution Microscopy. PLoS one. Dec. 29, 2014;9(12):e115512, pp. 1-20.

Walters, BJ et al., "Advanced In Vivo Use of CRISPR/Cas9 and Anti-Sense DNA Inhibition for Gene Manipulation in the Brain," Frontiers in genetics, Jan. 12, 2016, vol. 6, Article 362, pp. 1-13; p. 6, col. 1, third paragraph. DOI: 10.3389/fgene.2015.00362.

Zetsche et al. Cpf1 is a single RNA-guided endonuclease of a class 2 CRISPR-Cas system. Cell 163:759-771 (2015).

Bottari et al. Application of FISH technology for microbiological analysis: current state and prospects. Appl Microbiol Biotechnol Dec. 2006; 73(3):485-94.

Donaldson, Julie G. Unit 4.3 Immunofluorescence Staining. Curr Protoc Cell Biol May 2001; 04; Unit 4.3. 9 pages.

Duose, et al. Configuring robust DNA strand displacement reactions for in situ molecular analyses. Nucleic Acids Res. Apr. 2012; 40(7): 3289-3298.

Duose et al. Supporting Information to: Configuring robust DNA strand displacement reactions for in situ molecular analyses. 2012. 5 pages.

Duose et al. Supporting Information to: Multiplexed and Reiterative Fluorescence Labeling via DNA Circuitry. Bioconjugate Chem 2010. 4 pages.

Feature Analysis of Claim 1 from Opposition to European Patent No. EP4108782B1 filed by NanoString Technologies Inc., dated Jul. 18, 2023. 1 page.

Goransson et al. Supplementary Data to: A Single Molecule Array for Digital Targeted Molecular Analyses. Nucleic Acids Research, vol. 37, Issue 1, 2009. 5 pages.

(56) References Cited

OTHER PUBLICATIONS

Gunderson, et al. Decoding Randomly Ordered DNA Arrays. Genome Res. 14:870-877, 2004.
Henegariu et al. Colour-changing karyotyping: an alternative to M-FISH/SKY. Nature Genetics 23, 263-264 (1999).
Huang et al., Super-resolution fluorescence microscopy, Annu Rev Biochem. 2009; 78: 993-1016, First published: Apr. 2, 2009.
"Hybridisation". Extract from Oxford Dictionary of Biochemistry and Molecular Biology, Second Edition, 2006. 4 pages.
Olejnik et al. Photocleavable aminotag phosphoramidites for 5'-termini DNA/RNA labeling. Nucleic Acids Research, 1998, vol. 26, No. 15, 3572-3576.
Opposition to European Patent No. EP4108782B1 filed by NanoString Technologies Inc., dated Jul. 18, 2023. 83 pages.
"Probe". Extract from Oxford Dictionary of Biochemistry and Molecular Biology, Second Edition, 2006. 4 pages.
Schubert et al. Analyzing proteome topology and function by automated multidimensional fluorescence microscopy. Nature Biotechnology, 2006. 9 pages.
Söderberg, O. et al., "Characterizing proteins and their interactions in cells and tissues using the in situ proximity ligation assay," Methods, 2008;45(3):227-32.
Stryer et al. Biochemistry, Fifth Edition. pp. 124-125. 2002.
U.S. Appl. No. 61/579,265, inventors Levner; Daniel et al., filed Dec. 22, 2011.
Veccham et al. A Non-perturbative pairwise-additive analysis of charge transfer contributions to intermolecular interaction energies. Physical Chemistry Chemical Physics, 2020. 48 pages.
Zhen, et al. Poly-FISH: a technique of repeated hybridizations that improves cytogenetic analysis of fetal cells in maternal blood. Prenat Diagn. 1998; 18(11):1181-5.
Nakano et al. Effects of Molecular Crowding on the Structures, Interactions, and Functions of Nucleic Acids. Chem. Rev. 2014, 114, 5, 2733-2758.
EP19180827.8 Extended European Search Report dated Dec. 17, 2019.
PCT/US2019/055434 International Search Report and Written Opinion dated Jan. 23, 2020.
AbouHaidar, et al., Non-enzymatic RNA Hydrolysis promoted by the combined catalytic activity of buffers and magnesium Ions. Verlag der Zeitschrift fur naturforschung. Tubingen. 1999; 54c: 542-548.
Achim et al., High-throughput spatial mapping of single-cell RNA-seq data to tissue of origin. Nature Biotechnology, vol. 33, No. 5, May 2015, p. 503-511.
Agaouglu et al. Ultra-sensitive microfluidic wearable strain sensor for intraocular pressure monitoring. Lab on a Chip, Issue 22, 2018; pp. 3471-3483.
Al-Attar et al., Clustered Regularly Interspaced Short Palindromic Repeats (CRISPRs ): The Hallmark of an Ingenious Antiviral Defense Mechanism in Prokaryotes, Bio Chem. (2011) vol. 392, Issue 4, pp. 277-289.
Altshuler D, Daly MJ, Lander ES. 2008. "Genetic mapping in human disease" Science 322: 881-8.
Amasino et al., Acceleration of nucleic acid hybridization rate by polyethylene glycol, Analytical biochemistry,vol. 152, No. 2, Feb. 1, 1986.
Ansari et al, Rioactivators: Transcription activation by non-coding RNA, Grit Rev Biochem Mol Bioi. 2009 ; 44(1 ): 50-61.
Arezi et al., Novel mutations in Moloney Murine Leukemia Virus reverse transcriptase increase thermostability through tighter binding to template-primer. Nucleic Acids Research 37(2) : 473-481 (Year: 2009).
Ascano., Identification of RNA-protein interaction networks using PAR-CLIP. Wiley interdisciplinary reviews. RNA 3.2 (Mar. 2012): 159-177, DOI:10.1002/wrna.1103.
Bakal C, Aach J, Church G, Perrimon N. 2007. "Quantitative morphological signatures define local signaling networks regulating cell morphology" Science 316: 1753-6.

Ball et al. Targeted and genome-scale methylomics reveals gene body signatures in human cell lines. Nat. Biotechnol 27:361-368 (2009).
Bang D, Church GM. 2008. "Gene synthesis by circular assembly amplification" Nat Methods 5:37-9.
Bao, et al. A Novel DNA Detection Method Based on Gold Nanoparticle Probes and Gene Chips. Acta Chimica Sinica No. 18, 2144-2148. 2009. English Abstract provided.
Beliveau, Brian J. et al., Versatile design and synthesis platform for visualizing genomes with Oligopaint FISH probes, National Academy of Sciences, vol. 109, No. 52, Dec. 11, 2012, pp. 21301-21306.
Beliveau, Brian J. et al., Visualizing Genomes with Oligopaint Fish Probes: In: "Current Protocols in Molecular Biology", Jan. 6, 2014, Wiley, New York, NY.
Beliveau, et al. Single-molecule super-resolution imaging of chromosomes and in situ haplotype visualization using olligopaint FISH probes. Nat Commun. 2015; 6:7147; Abstract, p. 3 [according to the posted document], Fig 1 and its legend; p. 4, Fig 2 and its legend; p. 6, Fig 3 and its legend.
Bell J. 2004. "Predicting disease using genomics" Nature 429: 453-6.
Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.
Bock, RM. Alkaline Hydrolysis of RNA. Methods in Enzymology 12 : 224-228 (Year: 1967).
Bouche et al., The effect of spermidine on endonuclease inhibition by agarose contaminants. Analytical biochemistry, Academic press, vol. 115, No. 1, Jul. 15, 1918, pp. 42-45.
Brenner, et al., Gene Expression analysis by massively parallel signature sequencing (MPSS) on microbead arrays. Nature Biotechnology 18.6 (Jun. 2000): 630-634, doi:10.1038/76469.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Brown et al., Review Article : In situ Hybridization with Riboprobes :An Overview for Veterinary Pathologists. Veterinary Pathology 35 : 159-167 (Year: 1998.
Cao, et al., In-situ Immuno-PCR to detect antigens. The Lancet 356 (Sep. 2000): 1002-1003.
Capodieci et al. "Gene expression profiling in single cells within tissue" Nature Methods, Sep. 14, 2005, 2(9) pp. 663-665.
Carroll, "A CRISPR Approach to Gene Targeting" 20(9) Molecular Therapy 1658-1660 (Sep. 2012).
Chen, et al., Expansion Microscopy. Science, Jan. 30, 2015; vol. 347, Issue 6221: 543-549.
Chen et al., Functional organization of the human 4D Nucleome, PNAS Jun. 30, 2015 112 (26) 8002-8007; first published Jun. 15, 2015.
Chen, et al., Nanoscale imaging of RNA with expansion microscopy. Nature Methods. Aug. 2016; vol. 13, No. 8: pp. 679-687.
Cheng, et al. Multiplexed Activation of Endogenous Genes by CRISPR-on, An RNA-Guided Transcriptional Activator System. Cell Research. vol. 23. No. 10. Oct. 1, 2013. pp. 1163-1171.
Chiang DY, Getz G, Jaffe DB, O'Kelly MJ, Zhao X, Carter SL, Russ C, Nusbaum C, Meyerson M, Lander ES. 2009. High-resolution mapping of copy-number alterations with massively parallel sequencing Nat Methods 6: 99-103. PMC ID: PMC2630795.
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Choi et ai. Programmable in situ amplification for multiplexed imaging of mRNA expression. Nature Biotechnology 28(11): 1208 (Year: 2010).
Choi, et al., Next-Generation in Situ Hybridization Chain Reaction: Higher Gain, Lower Cost, Greater Durability. ACS NANO 8.5 (May 2014): 4284-4294, XP055409053, US.
Choy et al. 2008. "Genetic analysis of human traits in vitro: drug response and gene expression in lymphoblasloid cell lines" PLoS Genet 4: e1000287. PMC ID: PMC2583954.

(56) References Cited

OTHER PUBLICATIONS

Chozinski, et al., Expansion microscopy with conventional antibodies and fluorescent proteins. Nature Methods. Jun. 2016; vol. 13, No. 6: pp. 485-491.
Christian et al. 2001. "Detection of DNA point mutations and mRNA expression levels by rolling circle amplification in individual cells" Proc Nall Acad Sci U SA 98: 14238-43. PMC ID: PMC64666.
Church et al. 2008. "High-Speed Imaging for DNA Sequencing" Biopholonics ( http://NWW.pholonics.com/Conlenl/ReadArticle.aspx? ArticleID=33989).
Church et al.; Center for Casual Consequences of Variation {CCV} "An NHGRI Center for Excellence in Genomic Science" http://ccv.med.harvard.edu; Wayback Machine {Jul. 3, 2011).
Church et al.; Center for Casual Consequences of Variation {CCV} "Our four Specific Aims" http://ccv.med.harvard. edu/specific_aims.htm; Wayback Machine {Aug. 13, 2011).
Church GM. 2006. "Genomes for all" Sci Am 294: 46-54.
Church; "Proposal for a Center for the determination of the Causal Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).
Clausson et al., Compaction of rolling circle amplification products increases signal integrity and signal-to-noise ratio. Scientific Reports, vol. 5. Jul. 23, 2015. p. 12317.
Cong et al.: Multiplex genome engineering using CRISPR/Cas systems. Science 339(6121):819-823 (2013).
Conze et al. "Single molecule analysis of combinatorial splicing" Nucleic Acids Research, Jun. 29, 2010, vol. 38, No. 16; e163.
Cookson W, Liang L, Abecasis G, Moffatt M, Lathrop M. 2009. "Mapping complex disease traits with global gene expression" Nat Rev Genet 10: 184-94.
CRISPR in the Lab: A Practical Guide [online]. Addgene. Sep. 4, 2014. Retrieved on Dec. 4, 2014. Retrieved from the Internet: URL: https://www.addgene.org/CRISPR/guide/.
Dasari, et al., Platform for Spatial Molecular Data by Vivek Dasari 1-7 Signature redacted Thesis Supervisor. (Aug. 2015) XP055559164, URL: http://dspace.mit.edu/bitstream/handle/1721.1/107103/971494098-MIT.pdf?sequence=1.
Davies et al. Crystal Structure of the ribonuclease H domain of HIV-1 Reverse Transcriptase.Science 252 :88 (Year: 1991).
De Bakker PI, Yelensky R, Pe'er I, Gabriel SB, Daly MJ, Altshuler D. 2005. "Efficiency and power in genetic associalior studies" Nat Genet 37: 1217-23.
Deng et al., Targeted bisulfite sequencing reveals changes in DNA methylation associated with nuclear reprogramming. Nat Biotechnol. 27 (4):353-360 (2009).
Dicarlo, et al. Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dirks et al., Triggered amplification by hybridization chain reaction, PNAS 101(43) : 15275 (Year: 2004).
Dixon et al. 2007. "A genome-wide association study of global gene expression" Nat Genet 39:1202-7.
Doillon, et al., Actin Filaments in Normal Dermis and During Wound Healing. The American Journal of Pathology 126.1 (1987): 164-170.
Duose, et al. Multiplexed and Reiterative Fluorescence Labeling via DNA Circuitry. Bioconjug Chem. Dec. 15, 2010; 21(12): 2327-2331.
Eberwine et al. 2001. "mRna expression analysis of tissue sections and single cells" J Neurosci 21: 8310-4.
Eid et al. 2009. "Real-time DNA sequencing from single polymerase molecules" Science 323: 133-8.
Eliscovich, et al., mRNA on the move: The road to its biological destiny. Journal of Biological Chemistry 288.28 (Jul. 2013): 20361-20368.
Emilsson et al. 2008; "Genetics of gene expression and its effect on disease" Nature 452: 423-8.

Femino et al. "Visualization of Single RNA Transcripts in Situ" Science, Apr. 24, 1998, vol. 280, pp. 585-590.
Fu et al. Improving CRISPR-Cas nuclease specificity using truncated guide RNAs. Nat Biotechnol 32(3):279-284 (2013).
Gao, et al., An Efficient strategy for sequencing-by-synthesis. Journal of Nanoscience and nanotechnology. 2010; 10:2988-2993.
Gasiunas et al. Cas9-crRNA ribonucleoprotein complex mediates specific DNA cleavage for adaptive immunity in bacteria. PNAS USA 109:E2579-E2586 (2012).
Gavrilovic et al. "Automated Classification of Multicolored Rolling Circle Products in Dual-Channel Wide-Field Fluorescence Microscopy" Cytometry Part A, Jul. 2011, 79(7), pp. 518-527.
Geiss, et al. Direct multiplexed measurement of gene expression with color-coded probe pairs. Nat Biotechnol. Mar. 2008;26(3):317-25. doi: 10.1038/nbt1385. Epub Feb. 17, 2008.
Gilbert et al., CRISPR-Mediated modular RNA-guided regulation of transcription in Eukaryotes. Cell 154(2): 442-451 (2013).
Ginart, et al., RNA Sequencing In Situ. Nat Biotechnol 32.6 (Jun. 2014): 543-544, DOI:10.1038/nbt.2921.
Goransson et al.: A single molecule array for digital targeted molecular analyses. Nucleic Acids Res. 37(1):e7:1-9 doi:10.1093/nar/gkn921 (2009).
Grompe, The rapid detection of unknown mutations in nucleic acids. Nature Genetics (Oct. 1993): 111-117, DOI: 10.1038/ng1093-111.
Gunderson et al., Decoding randomly ordered DNA arrays. Genome Research. 14(5):870-877 (2004).
Guo et al. "Target-driven DNA association to initiate cyclic assembly of hairpins for biosensing and logic gate operation" Chemical Science, 2015, 6, pp. 4318-4323.
Gusev, et al., Rolling circle amplification: a new approach to increase sensitivity for immunohistochemistry and flow cytometry. Am J Pathol . Jul. 2001;159(1):63-9. doi: 10.1016/S0002-9440(10)61674-4.
Hale et al., Essential Features and Rational Design of CRISPR RNAs That Function With the Cas RAMP Module Complex to Cleave RNAs, Molecular Cell, (20 12) vol. 45, Issue 3, 292-302.
Han, et al., Quantum-dot-tagged microbeads for multiplexed optical coding of biomolecules. Nature Biotechnology 19.99 (Jul. 2001): 631-635.
Hansen et al., Sensitive ligand-based protein quantification using immuno-PCR: A critical review of single-probe and proximity ligation assays. Biotechniques 56:217-228 (Year: 2014).
Harris et al. 2008. "Single-molecule DNA sequencing of a viral genome" Science 320: 106-9.
Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.
Ho et al. "Sequencing by ligation variation with endonuclease V digestion and deoxyinosine-containing query oligonucleotides" BMC Genomics, 2011, 12:598.
International HapMap C. 2005. "A haplotype map of the human genome" Nature 437: 1299-1320. PMCID: PMC1880871.
Itzkovitz et al. "Single molecule transcript counting of stem cell markers in the mouse intestine" Nat Cell Biol., Nov. 2011, 14(1), pp. 106-114.
Itzkovitz et al., Validating transcripts with probes and imaging technology. Nat Methods. 8(4 Suppl):S12-9 (2011).
J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.
Jambhekar, et al., Cis-acting Determinants of Asymmetric, Cytoplasmic RNA Transport. RNA 13 (2007): 625-642.
Jarvius et al. Digital quantification using amplified single-molecule detection. Nat Methods 3:725-727 (2006).
Jiang et al. "Solar thermal polymerase chain reaction for smartphone-assisted molecular diagnostics" Scientific Reports, 4:4137, 2014.
Jinek , et al. 'RNA-programmed genome editing in human cells.' eLite 2013;2:e00471 . [retrieved 1-3, 6, 7, 10-12 on Jun. 3, 2014).

(56) References Cited

OTHER PUBLICATIONS

Retrieved from the Internet. URL: http://elife.elifesciences.org/content/2/e00471 . entire document.
Jinek et al. A programmable dual-RNA-guided DNA endonuclease in adaptive bacterial immunity. Science 337(6096):816-821 (2012).
Ju et al. Four-Color DNA Sequencing by Synthesis Using Cleavable Fluorescent Nucleotide Reversible Terminators. PNAS USA 103:19635-19640 (2006).
Kalivas, et al., FamRCA-RACE: a Rolling Circle Amplification Race for Isolating a Family of Homologous CDNAS in One Reaction and Its Application to Obtain Nac Genes Transcription Factors From Crocus (*Crocus sativus*) Flower. Preparative Biochemistry and Biotechnology 40.3 (Jul. 2010): 177-187.
Ke et al., In situ sequencing for RNA analysis in preserved tissue and cells. Nature Methods 10(9): 857 (Year: 2013).
Kim JB, Porreca GJ, Song L, Greenway SC, Gorham JM, Church GM, Seidman CE, Seidman JG. 2007. "Polony multiplex analysis of gene expression (PMAGE) in mouse hypertrophic cardiomyopathy" Science 316: 1481-4.
Klein RJ. 2007. "Power analysis for genome-wide association studies" BMC Genet 8: 58. PMC ID: PMC2042984.
Kolb HC, Finn MG, B. SK. 2001. "Click Chemistry: Diverse Chemical Function from a Few Good Reactions" Angew.Chem. Int. 40: 2004-21.
Koller, et al., Mechanisms of single-stranded phosphorothioate modified antisense oligonucleotide accumulation in hepatocytes. Nucleic Acids Research, 2011, vol. 39, No. 11, 4795-4807.
Kotewicz et al., Isolation of MMuLV RT lacking RNase H activity. Nucleic Acids Research 16(1) :265 (Year: 1988).
Kuimelis et al., Cleavage properties of an oligonucleotide containing a bridged internucleotide 5-phosphorothioate RNA linkage. Nucleic Acids Research 23 (23) : 4753-4760 (Year: 1995).
Kurimoto et al. 2007. "Global single-cell cDNA amplification to provide a template for representative high-density oligonucleotide microarray analysis" Nat Protoc 2: 739-52.
Kuznetsova et al: "What Macromolecular Crowding Can Do to a Protein". Int.J.Mol.Sci . . . vol. 15. No. 12. Dec. 1, 2014 (Dec. 1, 2014). pp. 23090-23140.
Kwan et al. 2008. "Genome-wide analysis of transcript isoform variation in humans" Nat Genet 40: 225-31.
Kwiatkowski et al. 1999. "Inversion of in situ synthesized oligonucleolides: improved reagents for hybridization and primer extension in DNA microarrays" Nucleic Acids Res 27: 1710-4. PMC ID: PMC148770.
Lagunavicius et al. "Novel application of Phi29 DNA polymerase: RNA detection and analysis in vitro and in situ by target RNA-primed RCA" RNA, May 2009, 15(5), pp. 765-771.
Larsson, et al., In situ detection and genotyping of individual mRNA molecules. Nature Methods, vol. 7, No. 5, Apr. 11, 2010. pp. 395-397.
Lee, et al., "Fluorescent in situ sequencing (FISSEQ) of RNA for gene expression profiling in intact cells and tissues" Nature Protocols (Feb. 12, 2015) 10(3):442-458. XP055272042, GB ISSN:1754-2189, DOI: 10.1038/nprot.2014.191.
Lee, et al., Highly Multiplexed Subcellular RNA Sequencing in Situ. Science 343.6177 (Mar. 2014): 1360-1363, doi: 10.1126/science.1250212.
Leman, AR et al. The Replication Fork: Understanding the Eukaryotic Replication Machinery and the Challenges to Genome Duplication. Genes. Jan. 29, 2013. vol. 4; pp. 1-32; figure 1; DOI: 10.3390/genes4010001.
Leuchowius, Karl-Johan et al. Parallel Visualization of Multiple Protein Complexes in Individual Cells in Tumor Tissue. The American Society for Biochemistry and Molecular Biology, Inc. Molecular & Cellular Proteomics vol. 12, No. 6, pp. 1563-1571. Jun. 2013.
Levsky et al. "Fluorescence in situ hybridization: past, present and future" Journal of Cell Science, Jul. 15, 2003, 116 (Pt 14), pp. 2833-2838.
Levsky et al. "Single-Cell Gene Expression Profiling" Science, Aug. 2, 2002, 297(5582), pp. 836-840.

Li and Beaker. Kinetics of RNA Degradation by Specific Base Catalysis of Transesterification Involving the 2'-Hydroxyl Group. JACS 121 :5364 (Year: 1999).
Li et al. 2009. "Genome-wide Identification of Human RNA Editing Sites by Parallel DNA Capturing and Sequencing" Science in press.
Li et al. 2009. "Multiplex padlock capture and sequencing reveal human hypermulable CpG variations" Genome Res in press.
Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).
Liu et al, Cell-Penetrating Peptide-Mediated Delivery of TALEN Proteins via Bioconjugation for Genome Engineering, PLOS One, 2014, vol. 9(1), pp. 1-7.
Lizardi, Next-generation sequencing-by-hybridization. Nature Biotechnology, vol. 26, No. 6, Jun. 2008, pp. 649-650.
Lubeck et al. Single cell systems biology by super-resolution imaging and combinatorial labeling. Nat Methods; 9(7): 743-748. Jan. 1, 2013.
Lubeck et al., Single-cell in situ RNA profiling by sequential hybridization. Mar. 2014, Nature Methods vol. 11, No. 4, pp. 360-361.
Maeder, Morgan L., et al.," Robust, synergistic regulation of human gene expression using TALE activators," HHS Public Access Author Manuscript, vol. 10, No. 3, Feb. 10, 2013 (Feb. 10, 2013), pp. 243-245.
Mag et al. Synthesis and selective cleavage of an oligodeoxynucleotide containing a bridged internucleotide 5'-phosphorothioate linkage. Nucleic Acids Res. 19, 7 (1991): 1437-1441.
Maierhofer et al. "Multicolor Deconvolution Microscopy of Thick Biological Specimens" American Journal of Pathology, vol. 162, No. 2, Feb. 2003, pp. 373-379.
Makarova, et al. Evolution and classification of the CRISPR-Cas systems. Nat Rev Microbiol. Jun. 2011;9(6):467-77. doi: 10.1038/nrmicro2577. Epub May 9, 2011.
Mali et al., RNA-Guided Human Genome Engineering via Cas9. Science, 339 (Feb. 15, 2013): 823-826.
Mali, P. et al. CAS9 Transcriptional Activators for Target Specificity Screening and Paired Nickases for Cooperative Genome Engineering. Nature Biotechnology. Aug. 1, 2013. vol. 31; pp. 833-838; entire document. DOI: 10.1038/nbt.2675.
Marblestone, et al., Rosetta Brains: A strategy for molecularly-annotated connectomics. arXiv, Apr. 2014; 1-18.
Markaki et al. "Fluorescence In Situ Hybridization Applications for Super-Resolution 3D Structured Illumination Microscopy" Methods in Molecular Biology, Jan. 2013, vol. 950, pp. 43-64.
Mathews, CK., Biochemistry of deoxyribonucleic acid-defective amber mutants of bacteriophage T4. Journal of Biological Chemistry 243(21) :5610-5615. (Year: 1968).
Matlin, et al., Spatial Expression of the Genome: the Signal Hypothesis at Forty. Nature Reviews. Molecular Cell Biology 12.5 (May 2011): 333-340.
Mccarroll SA. 2008. "Extending genome-wide association studies to copy-number variation" Hum Mol Genet 17: R135-42.
Meade et al. "Multiplexed DNA detection using spectrally encoded porous" Analytical Chemistry, Apr. 1, 2009, 81(7), pp. 2618-2625.
Meeks, et al., Characterization of Genes Encoding Poly(a) Polymerases in Plants: Evidence for Duplication and Functional Specialization. Plos One 4.11 (Nov. 2009): e8082.
Mei, et al., A comprehensive review and performance evaluation of bioinformatics tools for HLA class I peptide-binding prediction. Briefings in bioinformatics, 00(00), 2019, 1-17.
Meng Q, Kim DH, Bai X, Bi L, Turro NJ, Ju J_ 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.
Mignardi et al. "Fourth-generation sequencing in the cell and the clinic" Genome Medicine, 2014, 6:31.
Mitra et al. 2003. "Digital genotyping and haplotyping with polymerase colonies" Proc Nall Acad Sci US A 100: 5926-31. PMC ID: PMC156303.
Mitra et al. 2003. "Fluorescent in situ sequencing on Jolymerase colonies" Anal Biochem 320: 55-65.

(56) References Cited

OTHER PUBLICATIONS

Mitra et al.: In situ localized amplification and contact replication of many individual DNA molecules. Nucleic Acids Res. 27(24):e34 (1999).
Monika S Rutowska et al: "Integration of a 3D hydrogel matrix with a hollow core photonic crystal fibre for DNA probe immobilization", Measurement Science and Technology, IOP, Bristol, GB, vol. 21, No. 9, Jul. 28, 2010 (Jul. 28, 2010), p. 94016, XP020197365,ISSN: 0957-0233, DOI: 10.1088/0957-0233/21 /9/094016.
Morley M, Molony CM, Weber TM, Devlin JL, Ewens KG, Spielman RS, Cheung VG. 2004. "Genetic analysis of Genome-wide variation in human gene expression" Nature 430: 743-7.
Muller et al. Towards unlimited colors for fluorescence in-situ hybridization (FISH). Chromosome Research. 10:223-232, 2002.
Nadji et ai. "Photochemically and Photoenzymatically Cleavable DNA," J. Am. Chern. Soc. 1992, 114, 9266-9269.
Nair, S. et al., Natural Killer T cells in cancer immunotherapy. Front. Immunol. Sep. 2017; 8(1178): 1-18.
Ng L et al: "Surface-based mapping of gene expression and probabilistic expression maps in the mouse cortex", Methods, Academic Press, NL,vol. 50, No. 2, Feb. 1, 2010 (Feb. 1, 2010), pp. 55-62, XP026857255,ISSN: 1 046-2023.
Nguyen, Son C.: "Strategies for Studying Chromatin Regulation and Organization", May 1, 2018 (May 1, 2018). XP055684323. Retrieved from the Internet: URL: https://dash.harvard.edu/bitstream/handle/1/33493431/NGUYEN-DISSERTATION-2016.pdf?sequence=4&isAllowed=y [retrieved on Apr. 8, 2020].
Nikolakakis, K. et al., Use of Hybridization Chain Reaction-Fluorescent In Situ Hybridization to Track Gene Expression by Both Partners during Initiation of Symbiosis. Appl Environ Microbiol . Jul. 2015;81(14):4728-35. doi: 10.1128/AEM.00890-15. Epub May 8, 2015.
Nuovo, G.J., Co-labeling Using In Situ PCR: A Review, Journal of Histochemistry & Cytochemistry. vol. 49. No. 11, Nov. 1, 2001 (Nov. 1, 2001). pp. 1329-1339.
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Oupicky David et al: "Laterally stabilized complexes of DNA with linear reducible polycations: Strategy for triggered intracellular activation of DNA delivery vectors". Journal of the American Chemical Society. American Chemical Society. US. vol. 124. No. 1. Jan. 9, 2002 (Jan. 9, 2002). pp. 8-9.
Pan et al. 2008. "A procedure for highly specific, sensitive, and unbiased whole-genome amplification" Proc Nall Acad Sci US A 105: 15499-504. PMC ID:PMC2563063.
Parinov et al. "DNA sequencing by hybridization to microchip octa- and decanucleotides extended by stacked pentanucleotides" Nucleic Acids Research, 1996, vol. 24, No. 15, pp. 2998-3004.
Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.
Philipp Spuhler et al: "Precise control of DNA orientation for improved functionality in protein binding microarrays", Optical MEMS and Nanophotonics (OMN), 2011 Internationalconference on, IEEE, Aug. 8, 2011 (Aug. 8, 2011), pp. 91-92,XP031968753,DOI: 10.1109/0MEMS.2011.6031084ISBN: 978-1-4577-0334-8.
PI: Piezo Nano Positioning, 2008 (online), retrieved on Aug. 12, 2020, pp. 1-6 https://www.pi -usa.us/fileadmin/user_upload/pi_us/files/product_datasheets/N725_Piezo_Focus_Positioner.pdf.
Pihlak, et al. Rapid genome sequencing with short universal tiling probes. Nature Biotechnology, 26: 676-684 (2008).
Pjanic et al. "Nuclear Factor I genomic binding associates with chromatin boundaries," BMC Genomics, Feb. 12, 2013 {Feb. 12, 2013), vol. 14, No. 99, pp. 1-18. entire document.
Polidoros, et al., Rolling circle amplification-RACE: A method for simultaneous isolation of 5' and 3' cDNA ends from amplified cDNA templates. BioTechniques 41.1 (Jul. 2006):35-42. including p. 1/1 of Supplementary Material.
Porreca et al. 2006. "Polony DNA sequencing" Curr Protoc Mol Biol Chapter 7: Unit 7.8; Supplement 76: 22 Pages.
Porreca et al. 2007. "Multiplex amplification of large sets of human exons" Nat Methods 4: 931-6.
Qi et al. Repurposing CRISPR as an RNA-guided platform for sequence-specific control of gene expression. Cell 152:1173-1183 (2013).
Raj et al. Imaging individual mRNA molecules using multiple singly labeled probes. Nature Methods 5(10):877-879 (2008).
Ramakrishna et al. Gene disruption by cell-penetrating peptide-mediated delivery of Cas9 protein and guide RNA. Genome Research 24:1020-1027 (2014).
Ran, et al. Double Nicking by RNA-Guided CRISPR Cas9 for Enhanced Genome Editing Specificity. Cell. Aug. 28, 2013. pii: S0092-8674(13)01015-5. doi: 10.1016/j.cell.2013.08.021. [Epub ahead of print].
Ravan, et al., Isothermal RNA Detection Through the Formation of DNA Concatemers Containing HRP-mimicking DNAzymes on the Surface of Gold Nanoparticles. Biosensors and Bioelectronics 80 (Jan. 2016): 67-73.XP029441324.
Rho, Mina et al. 'Diverse CRISPRs Evolving in Human Microbiomes.' PLoS Genetics. vol. 8, No. 6. 1-14 pp. 1-12. Jun. 2012. entire document.
Richardson et al., Experimental and Theoretical Studies of Light-to-Heat Conversion and Collective Heating Effects in Metal Nanoparticle Solutions. Nano Letters 9(3) : 1139-1146 (Year: 2009).
Risch N, Merikangas K. 1996. "The future of genetic studies of complex human diseases" Science 273: 1516-7.
Sachidanandam et al. 2001. "A map of human genome sequence variation containing 1.42 million single nucleotide polymorphisms" Nature 409: 928-33.
Saliba, et al., Single-cell RNA-Seq: Advances and Future Challenges. Nucleic Acids Research 42.14 (2014): 8845-8860, DOI: 10.1093/nar/gku555.
Sano, et al. Immuno-PCR: Very sensitive antigen detection by means of specific antibody-DNA conjugates. Science. 258 (1992): 120-122.
Sapranauskas et al. The *Streptococcus thermophilus* CRISPR/Cas system provides immunity in *Escherichia coli*. Nucleic Acid Res. 39:9275-9282 (2011).
Schadt et al. 2003. "Genetics of gene expression surveyed in maize, mouse and man" Nature 422: 297-302.
Schadt et al. 2008. Mapping the genetic architecture of gene expression in human liver PLoS Biol 6: e107. PMC ID: PMC2365981.
Schouten et al., "Relative quantification of 40 nucleic acid sequences by multiplex ligation-dependent probe amplification," Nucleic Acids Research, 30(12):e57, 2002.
Schweitzer et al. Immunoassays with rolling circle DNA amplification: a versatile platform for ultrasensitive antigen detection. Proceedings of the National Academy of Sciences. USA. 97(18) (Aug. 2000):10113-10119.
Seo, et al. Four-color DNA sequencing by synthesis on a chip using photocleavable fluorescent nucleotides. Proceeding of the National Academy of Sciences USA. 102.17 (Apr. 2005): 5926-5931.
Serre et al. 2008. "Differential allelic expression in the human genome: a robust approach to identify genetic and epigenetic cis-acting mechanisms regulating gene expression" PLoS Genet 4: e1000006. PMC ID: PMC2265535.
Shendure et al. 2004. "Advanced sequencing technologies: methods and goals" Nat Rev Genet 5: 335-44.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/Science.1117839.
Shendure JA, Porreca GJ, Church GM. 2008. "Overview of DNA sequencing strategies" Curr Protec Mol Biol Chapter 7: Unit 7.1; Supplement 81: 11 Pages.
Singer-Kruger, et al., Here, There, Everywhere. RNA Biology 11.8 (Aug. 2014): 1031-1039.
Soderberg, et al., Direct Observation of Individual Endogenous Protein Complexes in Situ by Proximity Ligation. Nature Methods 3.12 (Dec. 2006): 995-1000.

(56) References Cited

OTHER PUBLICATIONS

Song et al., Hybridization chain reaction-based aptameric system for the highly selective and sensitive detection of protein. Analyst 137: 1396 (Year: 2012).
Sontheimer et al., "Project 7: Establishing RNA-Directed DNA Targeting in Eukaryotic Cells; Project dates: Nov. 16, 2011 to Dec. 31, 2012" (Feb. 4, 2012).
Srinivas et al., On the biophysics and kinetics of toehold-mediated DNA strand displacement. Nucleic Acids Research 41 (22) : 10641-10658 (Year: 2013).
Starnes et al., Human immunodeficiency virus reverse transcriptase-associated RNase H Activity. J. of Biological Chemistry 264(12) : 7073-7077 (Year: 1989).
Stougaard et al. 2007. "In situ detection of non-polyadenylated RNA molecules using Turtle Probes and target primed rolling circle PRINS" BMC Biotechnol 7: 69. PMC ID: PMC2203993.
Sun et al. "Composite Organic-Inorganic Nanoparticles as Raman Labels for Tissue Analysis" Nano Letters, Feb. 2007, vol. 7, No. 2, pp. 351-356.
Supplemental Material for Schweitzer et al. (PNAS 2000; 97(18):10113-10119) (Year: 2000).
Tang et al. 2009. "mRNA-Seq whole-transcriptome analysis of a single cell" Nat Methods 6: 377-82.
Terry R, Porreca G, McCarthy K, Church GM. 2008. Polonator Instrument http://www.polonator.org ; Wayback Machine(Aug. 7, 2008) "Software".
Terry R, Porreca G, McCarthy K, Church GM. 2008. Polonator Instrument http://www.polonator.org; Wayback Machine (Sep. 5, 2008) "PET {Paired End-Tag) Genomic Shotgun Library Construction Protocol".
Terry R, Porreca G, McCarthy K, Church GM. 2008. Polonator Instrument http://www.polonator.org; Wayback Machine(Aug. 7, 2008) "Flow Cells".
Terry R, Porreca G, McCarthy K, Church GM. 2008. Polonator Instrument http://www.polonator.org; Wayback Machine(Aug. 7, 2008) "Instrument Overview".
Terry R, Porreca G, McCarthy K, Church GM. 2008. Polonator Instrument http://www.polonator.org; Wayback MachineAugust 7, 2008) "Open, Affordable, Sequencing ___".
Terry R, Porreca G, McCarthy K, Church GM. 2008. Polonator Instrument http://www.polonator.org; Wayback Machine(Aug. 7, 2008) "Protocols".
Terry R, Porreca G, McCarthy K, Church GM. 2008. Polonator Instrument http://www.polonator.org; Wayback Machine(Aug. 7, 2008) "Reagent Kits".
Terry R, Porreca G, McCarthy K, Church GM. 2008. Polonator Instrument http://www.polonator.org; Wayback Machine(Aug. 7, 2008) "The Polonator Ecosystem".
Terry R, Porreca G, McCarthy K, Church GM. 2008. Polonator Instrument http://www.polonator.org; Wayback Machine(Aug. 7, 2008) "The Vision".
Terry R, Porreca G, McCarthy K, Church GM. 2008. Polonator Instrument http://www.polonator.org; Wayback Machine(Jul. 5, 2008) "Polony Sequence Protocols".
Terry R, Porreca G, McCarthy K, Church GM. 2008. Polonator Instrument http://www.polonator.org; Wayback Machine(Sep. 5, 2008) "Bead Capping Protocol".
Terry R, Porreca G, McCarthy K, Church GM. 2008. Polonator Instrument http://www.polonator.org; Wayback Machine(Sep. 5, 2008) "Bead Enrichment Protocol".
Terry R, Porreca G, McCarthy K, Church GM. 2008. Polonator Instrument http://www.polonator.org; Wayback Machine(Sep. 5, 2008) "Coverslip Aminosilanation and Arraying Protocol".
Terry R, Porreca G, McCarthy K, Church GM. 2008. Polonator Instrument http://www.polonator.org; Wayback Machine(Sep. 5, 2008) "Emulsion Breaking Protocol".
Terry R, Porreca G, McCarthy K, Church GM. 2008. Polonator Instrument http://www.polonator.org; Wayback Machine(Sep. 5, 2008) "Emulsion PCR Protocol".
Terry R, Porreca G, McCarthy K, Church GM. 2008. Polonator Instrument http://www.polonator.org; Wayback Machine(Sep. 5, 2008) "Emulsion PCR/Bead Capping Kits".
Terry R, Porreca G, McCarthy K, Church GM. 2008. Polonator Instrument http://www.polonator.org; Wayback Machine(Sep. 5, 2008) "Enrichment Kits".
Terry R, Porreca G, McCarthy K, Church GM. 2008. Polonator Instrument http://www.polonator.org; Wayback Machine(Sep. 5, 2008) "Help Wanted".
Terry R, Porreca G, McCarthy K, Church GM. 2008. Polonator Instrument http://www.polonator.org; Wayback Machine(Sep. 5, 2008) "Paired-Leg Library Kits".
Terry R, Porreca G, McCarthy K, Church GM. 2008. Polonator Instrument http://www.polonator.org; Wayback Machine(Sep. 5, 2008) "Polony Sequence by Ligation Protocol".
Terry R, Porreca G, McCarthy K, Church GM. 2008. Polonator Instrument http://www.polonator.org; Wayback Machine(Sep. 5, 2008) "Run Kits".
The Delivery Problem, Nature Biotechnology, 2006, vol. 24(3), pp. 305-306.
Thisse et al., High-resolution in Situ Hybridization to Whole-mount Zebrafish Embryos. Nature Protocols 3.1 (2008): 59-69, Doi:10.1038/nprot.2007.514.
Tiley, LS et al. The VP16 Transcription Activation Domain Is Functional When Targeted to a Promoter-Proximal RNA Sequence. Genes and Development. 1992. vol. 6; pp. 2077-2087; abstract; p. 2077, first column, first paragraph.
Tillberg, et al., Protein-retention expansion microscopy of cells and tissues labeled using standard fluorescent proteins and antibodies. Nat Biotechnol . Sep. 2016;34(9):987-92. doi: 10.1038/nbt.3625. Epub Jul. 4, 2016.
Trafton, A. Editing the Genome With High Precision [online]. MIT News office. Jan. 3, 2013 [retrieved on Dec. 4, 2014). Retrieved from the Internet: URL: https://news.mit.edu/2013/editing-the-genome-with-high-precision-0103 ;pp. 1-3; p. 3, third paragraph.
Tsaflaris, et al., Isolation of Three Homologous AP1-like MADS-box Genes in Crocus (*Crocus sativus* L.) and Characterization of Their Expression. Plant Science 166.5 (May 2004): 1235-1243.
Vigneault F, Sismour AM, Church GM. 2008."Efficient microRNA capture and bar-coding via enzymatic oligonucleotide adenylation" Nat Methods 5: 777-9.
Wang, et al., Rapid and Sensitive detection of severe acute respiratory syndrome coronavirus by rolling circle amplification, 2005,43, 2339-2344.
Wang, et al. RNA-Seq: a revolutionary tool for transcriptomics. Nature Reviews Genetics, 10: 57-63 (2009).
Wang et al., "The method of axial drift compensation of laser differential confocal microscopy based on zero-tracking," Proc. of SPIE, vol. 9618, 96180X (2015).
Wählby et al. Sequential immunofluorescence staining and image analysis for detection of large numbers of antigens in individual cell nuclei. 47(1):32-41 (2002).
Weibrecht, et al., Simultaneous Visualization of Both Signaling Cascade Activity and End-Point Gene Expression in Single Cells, PLOS One. vol. 6. No. 5, May 25, 2011. p. e20148.
Weis, et al., Protein Targeting to Subcellular Organelles via mRNA Localization. Biochimica et Biophysica Acta 1833 available online (Apr. 2012): 260-273.
Wiedenheft et al. RNA-guided genetic silencing systems in bacteria and archaea. Nature 482:331-338 (2012).
Wilson et al. "Encoded Microcarriers for High-Throughput Multiplexed Detection" Angewandte Chemie International Edition, Sep. 18, 2006, 45(37), pp. 6104-6117.
Wright et al., "Dynamic closed-loop system for focus tracking using a spatial light modulator and a deformable membrane mirror," Optics Express, vol. 14, No. 1, pp. 222-228 (Jan. 9, 2006).
Wu et al . . . , "3'-o-modified Nucleotides as Reversible Terminators for Pyrosequencing," PNA, 2007, vol. 104(42), pp. 16462-16467.
Xiao et al., "Single-step Electronic Detection of Femtomolar DNA by Target-induced Strand Displacement in an Electrode-bound Duplex," PNAS, 2006, vol. 103(45), pp. 16677-16680.
Yamaguchi et al. "eDNA display: a novel screening method for functional disulfide-rich peptides by solid-phase synthesis and sta-

(56) References Cited

OTHER PUBLICATIONS bilization of mRNA-protein fusions," Nucleic Acids Research, Jun. 15, 2009 {Jun. 15, 2009), vol. 37, No. 16, e108 {p. 1-13 for citations). entire document.
Zhang et al. 2006. "Long-range polony haplotyping of individual human chromosome molecules" Nat Genet 38: 382-7.
Zhang et al., "Digital RNA Allelotyping Reveals Tissue-specific and Allele-specific Gene Expression in Human," Nat Methods., Aug. 2009, vol. 6(8), pp. 613-618.
Zhang et al., Dynamic DNA nanotechnology using strand-displacement reactions. Nature Chemistry 3 : 103-113 (Year: 2011).
Zhang et al., "Sequencing Genomes From Single Cells by Polymerase Cloning," Nature Biotechnology, 2006, vol. 24(6), pp. 680-686.
Zhao et al. "Advances of multiplex and high throughput biomolecular detection technologies based on encoding microparticles" Science China Chemistry, Aug. 2011, vol. 54, No. 8, pp. 1185-1201.
Zhao et al., An electrochemical aptasensor based on hybridization chain reaction with enzyme-signal amplification for interferon-gamma detection. Biosensors and Bioelectronics 36: 129-134 (Year: 2012).
Zhou, et al., In Situ detection of Messenger RNA using digoxiogenin-labeled oligonucleotides and rolling circle amplification. Experimental and molecular Pathology, 2001; 70: 281-288.
Abramoff, Michael, et al. Image Processing with ImageJ. Biophotonics International. vol. 11, Issue No. 7 (2003): 36-42.
Bioptechs, FCS2 (Focht Live-Cell Chamber System) Instructions (2007): 1-6. Retrieved on URL: http://www.bioptechs.com/Instructions/FCS2_i/fcs2-3_i.htm.
Brileya, Kristen, et al. Biofilm Growth Mode Promotes Maximum Carrying Capacity and Community Stability During Product Inhibition Syntrophy. Frontiers in Microbiology. vol. 5, Article No. 693 (2014): 1-14.
Bui, Duy, et al. Analytical Devices Based on Light-emitting Diodes—a Review of the State-of-the-art. Analytica Chimica Acta. vol. 853 (2015): 46-58.
Chirieleison, Steven, et al. Automated Live Cell Imaging Systems Reveal Dynamic Cell Behavior. Biotechnology Progress. vol. 27, Issue No. 4 (2011): 913-924.
Delaune, Emilie, et al. Single-cell-resolution Imaging of the Impact of Notch Signaling and Mitosis on Segmentation Clock Dynamics. Developmental Cell. vol. 23, Issue No. 5 (2012): 995-1005.
Ehrlicher, Allen, et al. Optical Neuronal Guidance. Methods in Cell Biology. vol. 83 (2007): 495-520.
Fang-Yen, Christopher, et al. Video-rate Tomographic Phase Microscopy. Journal of Biomedical Optics. vol. 16, Issue No. 1 (2011): 011005-1-011005-5.
Femino, Andrea M, et al. Visualization of Single Molecules of mRNA in Situ. Methods in Enzymology. vol. 361 (2003): 245-304.
Fischer, Robert, et al. Microscopy in 3D: a Biologist's Toolbox. Trends in Cell Biology. vol. 21, Issue No. 12 (2011): 682-691.
FluoSpheres™ Carboxylate-Modified Microspheres. Thermo Fischer Scientific. Retrieved from: https://www.thermofisher.com/order/catalog/product/F8809. (2024).
Gerhardt, Ilja, et al. Detection of Single Molecules Illuminated by a Light-emitting Diode. Sensors. vol. 11, Issue No. 1 (2011): 905-916.
Hamilton, HVXM 8-5 Valve Laboratory Products. Retrieved from URL on Mar. 7, 2024: https://www.hamiltoncompany.com/laboratoryproducts/valves/36766.
Harvard Apparatus, PHD 22/2000 Syringe Pump Series User's Manual, (1996).
Hattori, Akifumi , et al. Single-molecule Imaging With an Inexpensive UV-LED Light Source. Chemistry Letters. vol. 38, Issue No. 3 (2009): 234-235.
Hodneland, Erlend, et al. CellSegm—a MATLAB Toolbox for High-throughput 3D Cell Segmentation. Source Code for Biology and Medicine. vol. 8, Issue No. 16 (2013): 1-24.
James, Paul, Water Objectives a Personal Exploration . . . all is Not What It Seems. Microscopy UK 1-8 (2004). Retrieved from URL: http://www.microscopy-uk.org.uk/mag/indexmag.html? http://www.microscopy-uk.org.uk/mag/artoct04/pjwater.html.
Kuo, Jason, et al. High-power Blue/UV Light-emitting Diodes as Excitation Sources for Sensitive Detection. vol. 25, Issue No. 21-22 (2004): 3796-3804.
Moffit, et al. RNA Imaging With Multiplexed Error-Robust. Methods in Enzymology.vol. 572 (2016): 1-49.
Nikon MicroscopyU, Culture Chambers for Live-Cell Imaging, Retrieved from: https://web.archive.org/web/20150810165805/http://www.microscopyu.com:80/articles/livecellimaging/culturechambers.html. (2015).
Niman, Cassandra, et al. Controlled Microfluidic Switching in Arbitrary Time-sequences With Low Drag. Lab on a Chip. vol. 13 (2013): 2389-2396.
North, Alison J, Seeing is Believing? A Beginners' Guide to Practical Pitfalls in Image Acquisition. The Journal of Cell Biology. vol. 172, Issue No. 1 (2006) :9-18.
O'Connor, Clare, Fluorescence In Situ Hybridization (FISH). Nature Education. vol. 1, Issue No. 1 (2008). Retrieved from URL: https://www.nature.com/scitable/topicpage/fluorescence-in-situ-hybridization-fish-327.
Olympus Lifescience, Instructions IX71/IX51 Inverted Research Microscope/Inverted Basic Microscope, (2005) at https://www.ucc.ie/en/media/academic/anatomy/imagingcentre/icdocuments/OLYMPUSIX71_manual.pdf.
Olympus Lifescience, Inverted Research System Microscopes IX71/IX81 IX2 Series Manual Olympus IX-71 (2009). Retrieved from: https://afns-labs.ualberta.ca/wp-content/uploads/sites/58/2018/05/Olympus-IX81-brochure.pdf.pdf.
Olympus Lifescience. Research Inverted System Microscope IX71/IX81 IX2 Series (2005), Retrieved from: https://www.olympus-lifescience.com/data/olympusmicro/brochures/pdfs/ix71.pdf?rev=EABE.
Pedersen, Peder Skafte, et al. A Self-contained, Programmable Microfluidic Cell Culture System With Real-time Microscopy Access. Biomedical Microdevices. vol. 14, Issue No. 2 (2012): 385-399.
Perillo, Evan P, et al. Enhanced 3D Localization of Individual RNA Transcripts via Astigmatic Imaging (2014). SPIE Conference Proceedings. vol. 8950 (2014): 895003-1 895003-11.
Querido, Emmanuelle, et al. Using Fluorescent Proteins to Study mRNA Trafficking in Living Cells. Methods in Cell Biology. vol. 85 (2008): 273-292.
Richard, Marc J P, et al. Cellular Mechanisms by Which Lipoic Acid Confers Protection During the Early Stages of Cerebral Ischemia: a Possible Role for Calcium. Neuroscience Research. vol. 69, Issue No. 4 (2011): 299-307.
Sands, Gregory, et al. Automated Imaging of Extended Tissue Volumes Using Confocal Microscopy. Microscopy Research and Technique. vol. 67, Issue No. 5 (2005): 227-239.
Schneider, Caroline, et al. NIH Image to ImageJ: 25 Years of Image Analysis. Nature Methods. vol. 9, Issue No. 7 (2012): 671-675.
Shah, Sheel, et al. Dynamics and Spatial Genomics of the Nascent Transcriptome by Intron seqFISH. Cell. vol. 174, Issue No. 2 (2018): 363-376.
Shen, Feimo, et al. 32 Digital Autofocus Methods for Automated Microscopy. Methods in Enzymology. vol. 414 (2006): 620-632.
Sivaramakrishnan, Sivaraj, et al. Shear Stress Induced Reorganization of the Keratin Intermediate Filament Network Requires Phosphorylation by Protein Kinase C Zeta. Molecular biology of the cell. vol. 20, Issue No. 11 (2009): 2755-2765.
Spector, David L, et al. [75] Observation of Live Cells in the Light Microscope. Cells A Laboratory Manual. vol. 2 (1998):75.1-75.13.
Thermo Fischer Scientific, Fluorescence SpectraViewer, Retrieved on Feb. 29, 2024, from: https://www.thermofisher.com/order/fluorescence-spectraviewer/#!/.
Tirichine, Leïla, et al. 3D Fluorescent in Situ Hybridization Using Arabidopsis Leaf Cryosections and Isolated Nuclei. Plant Methods. vol. 5, Article 11 (2009): 1-7.
Toomre, Derek, et al. A New Wave of Cellular Imaging. Annual Review of Cell and Developmental Biology. vol. 26 (2010): 285-287.

(56) References Cited

OTHER PUBLICATIONS

U.S. Pat. No. 11,542,554—*Nanostring Technologies, Inc.* (Petitioner) v. *President and Fellows of Harvard College.* Petition for Inter Partes Review dated Jan. 30, 2024.
U.S. Appl. No. 17/395,534 Notice of Allowance dated Jun. 21, 2022.
U.S. Appl. No. 17/395,534 Office Action dated Mar. 4, 2022.
Wessels, Johannes, et al. Light-emitting Diodes in Modern Microscopy—from David to Goliath?. Cytometry. vol. 81, Issue No. 3 (2012): 188-197.
Winer, Michael, et al. Application of a Three-dimensional (3D) Particle Tracking Method to Microfluidic Particle Focusing. Lab on a Chip. vol. 14 (2014): 1443-1451.
Xiao, Jie, Single-Molecule Imaging in Live Cells. Handbook of Single-Molecule Biophysics (2009): 43-93.
Zessin, Patrick, et al. A Hydrophilic Gel Matrix for Single-molecule Super-resolution Microscopy. Optical Nanoscopy. vol. 2, Issue No. 4 (2013): 1-8.

THREE-DIMENSIONAL SPATIAL MOLECULAR INDEXING

CROSS-REFERENCE

This application is a continuation of International Application No. PCT/US19/55434 filed Oct. 9, 2019 which claims priority to U.S. Provisional Patent Application No. 62/743,836, filed Oct. 10, 2018, and U.S. Provisional Patent Application No. 62/853,876, filed May 29, 2019, each of which is entirely incorporated herein by reference.

BACKGROUND

Fluorescent in situ sequencing (FISSEQ) may be used to detect one or more fluorescent signals emanating from each sequencing template within a FISSEQ library over more than one cycle of fluorescence detection, wherein the fluorescent signals over the totality of detection cycles may comprise an information construct, which may be mapped to molecular identification or otherwise provide information about the nature of the detected molecule.

SUMMARY

The present disclosure provides methods and systems for determining locations of nucleic acid molecules in situ and determining sequencing of such nucleic acid molecules, in some cases at high sequencing depth.

For example, ribonucleic acid (RNA) may be converted into complementary deoxyribonucleic acid (cDNA) with the addition of a known accessory sequence domain, such as by using a reverse transcription primer with a known sequence domain on the 5' end of the primer, and the 3' end priming a reverse transcription reaction, such as by using a plurality of random sequences, such as hexamers, a poly-dT sequence, or another sequence. The cDNA molecules may be subsequently circularized, such as by a splint ligation or ssDNA circularization ligation (e.g., by CircLigase) reaction, and locally amplified, such as by rolling circle amplification (RCA), in situ within the 3D matrix. The amplified sequencing template may be subsequently subjected to fluorescent sequencing, such as by sequencing by hybridization (SBH), sequencing by synthesis (SBS), or sequencing by ligation (SBL) chemistries. In this manner, the spatial position and some or all of the sequence of the originating RNA molecule is determined.

In an aspect, the present disclosure provides a method for processing or analyzing a plurality of nucleic acid molecules of a cell or cell derivative, comprising: (a) generating in the cell or cell derivative a synthetic three-dimensional (3D) matrix having the plurality of nucleic acid molecules attached thereto, wherein the plurality of nucleic acid molecules have a relative 3D spatial relationship: (b) determining a 3D spatial position of each of at least a subset of the plurality of nucleic acid molecules in the synthetic 3D matrix: (c) subsequent to determining the 3D spatial position of each of at least a subset of the plurality of nucleic acid molecules, removing the at least the subset of the plurality of nucleic acid molecules or derivatives thereof from the synthetic 3D matrix; and (d) identifying a sequence of each of the at least the subset of the plurality of nucleic acid molecules or derivatives thereof.

In some embodiments, (b) comprises determining a sequence of each of the at least the subset of the plurality of nucleic acid molecules in the synthetic 3D matrix. In some embodiments, (b) comprises sequencing each of the at least the subset of the plurality of nucleic acid molecules in the synthetic 3D matrix. In some embodiments, (b) comprises using a plurality of probe molecules to determine the 3D spatial position.

In some embodiments, the plurality of probe molecules are used to determine a sequence of each of the at least the subset of the plurality of nucleic acid molecules. In some embodiments, the plurality of probe molecules is padlock probe molecules, molecular inversion probe molecules, reverse transpiration primers, or second strand synthesis primers. In some embodiments, the plurality of probe molecules are detection agents coupled to the at least subset of the plurality of nucleic acid molecules. In some embodiments, the detection agents are nucleic acid molecules. In some embodiments, the detection agents are proteins. In some embodiments, the proteins are antibodies or portions of the antibodies. In some embodiments, the 3D matrix comprises coupling agents that are configured to attach to the plurality of nucleic acid molecules or derivatives thereof. In some embodiments, a concentration of the coupling agents is less than a concentration of the plurality of nucleic acid molecules. In some embodiments, a concentration of the coupling agents is more than a concentration of the plurality of nucleic acid molecules. In some embodiments, a concentration of the coupling agents is substantially similar to a concentration of the plurality of nucleic acid molecules. In some embodiments, the coupling agents are primers or nucleotides.

In some embodiments, the plurality of nucleic acid molecules are a plurality of target nucleic acid molecules, which plurality of target nucleic acid molecules are endogenous nucleic acid molecules within the cell or cell derivative, or synthetic nucleic acid molecules. In some embodiments, the plurality of target nucleic acid molecules is attached to the 3D matrix through a plurality of index nucleic acid molecules. In some embodiments, the plurality of index nucleic acid molecules is attached to the 3D matrix.

In some embodiments, the plurality of nucleic acid molecules is a plurality of indices. In some embodiments, a concentration of the plurality of indices is less than or equal to about 900, 800, 600, 500, 400, 300, 200, or 100 molecules per cubic nanometers. In some embodiments, the plurality of indices is generated in situ simultaneously by immobilizing the plurality of indices or a portion thereof in the 3D matrix. In some embodiments, immobilizing the plurality of indices or a portion thereof comprises using an activatable immobilization chemistry. In some embodiments, the activatable immobilization chemistry is photoactivatable, thermally activatable, or chemically activatable. In some embodiments, the activatable immobilization chemistry is photoactivatable, and wherein the activatable immobilization chemistry comprises removing photolabile protecting groups attached to the plurality of indices or sub-segments thereof, triggering conformational change of compounds attached to the plurality of indices or sub-segments thereof, or triggering a change in local chemical environment by light. In some embodiments, the photolabile protecting groups are nitroveratryloxycarbonyl (NVOC), 2-nitrobenzyl-, 6-nitropiperonyl, or 9-anthrylmethyl groups. In some embodiments, the compounds are cyclic azobenzene derivatives. In some embodiments, the change in local chemical environment comprises using a photogenerated acid (PGA) trigger for deprotection of a 5'-OH group in nucleotide phosphoramidite monomers.

In some embodiments, the plurality of indices is synthesized in situ on the 3D matrix. In some embodiments, the plurality of indices is synthesized in situ on the 3D matrix using a polymerizing enzyme or a ligation enzyme. In some embodiments, the polymerizing enzyme is a deoxyribonucleic acid polymerase. In some embodiments, the ligation enzyme is a deoxyribonucleic acid ligase. In some embodiments, the plurality of indices is synthesized in situ on the 3D matrix via templated nucleic acid synthesis, un-templated nucleic acid synthesis, or partially templated nucleic acid synthesis. In some embodiments, the un-templated nucleic acid synthesis comprises using a terminal transferase. In some embodiments, a given set of the plurality of indices within a given unit of volume has a unique index sequence. In some embodiments, the given set of the plurality of indices within the given unit of volume is a clonal population of the unique index sequence. In some embodiments, the given unit of volume is a cubic nanometer. In some embodiments, the given unit of volume has a diameter from about 100 to 200 nanometers, from 200 to 300 nanometers, from 300 to 400 nanometers, from 400 to 500 nanometers, from 500 to 600 nanometers, or from 600 to 700 nanometers. In some embodiments, the clonal population is generated by amplification from a single index molecule. In some embodiments, the amplification is a rolling circle amplification (RCA), polymerase chain reaction (PCR), loop mediated isothermal amplification (LAMP), nucleic acid sequence based amplification (NASBA), self-sustained sequence replication (3SR), strand displacement amplification, or multiple displacement amplification.

In some embodiments, the clonal population of the unique index sequence comprises a plurality of amplicons, which plurality of amplicons comprises functional linkage groups for attaching to the 3D matrix. In some embodiments, the functional linkage groups are amino-allyl dUTP, 5-TCO-PEG4-dUTP, C8-Alkyne-dUTP, 5-Azidomethyl-dUTP, 5-Vinyl-dUTP, 5-Ethynyl dUTP, or a combination thereof. In some embodiments, the plurality of amplicons is fragmented. In some embodiments, the plurality of amplicons comprises dUTP, inosine, or a nucleotide analog having an internal cleavage site. In some embodiments, the plurality of amplicons is fragmented by Uracil-Specific Excision Reagents (USER) or endonuclease V. In some embodiments, the clonal population is generated by parallel synthesis. In some embodiments, the parallel synthesis comprises using photoactivated immobilization chemistry. In some embodiments, the plurality of indices are substantially structured or organized in a regular pattern. In some embodiments, the plurality of probe molecules targets the at least the subset of the plurality of nucleic acid molecules. In some embodiments, (a) comprises directing a precursor of the synthetic 3D matrix through the cell or cell derivative, and subjecting the precursor of the synthetic 3D matrix to polymerization or cross-linking to form the synthetic 3D matrix.

In some embodiments, the synthetic 3D matrix is immobilized on to a solid substrate. In some embodiments, the synthetic 3D matrix is a generated from chemical crosslinks or physical crosslinks. In some embodiments, the crosslinks are formed via free-radical polymerization, chemical conjugation or bioconjugation reactions. In some embodiments, the crosslinks are formed by photopolymerization. In some embodiments, the photopolymerization is initiated by single-photon or multiphoton excitation systems. In some embodiments, the photopolymerization is initiated by manipulation of light to form specific two-dimensional (2D) or 3D patterns. In some embodiments, the photopolymerization is initiated by a spatial light modulator. In some embodiments, the spatial light modulator is a digital spatial light modulator. In some embodiments, the spatial light modulator employs a transmissive liquid crystal, reflective liquid crystal on silicon (LCOS), digital light processing, or a digital micromirror device (DMD). In some embodiments, the plurality of nucleic acid molecules is attached to the synthetic 3D matrix by non-covalent interactions or covalent interactions. In some embodiments, the plurality of nucleic acid molecules is reversibly attached to the synthetic 3D matrix. In some embodiments, the plurality of nucleic acid molecules is released from the synthetic 3D matrix. In some embodiments, the cell or cell derivative is fixed with a chemical fixing agent. In some embodiments, the chemical fixing agent is formaldehyde or glutaraldehyde. In some embodiments, the synthetic three-dimensional matrix comprises a polymeric material. In some embodiments, the synthetic 3D matrix comprises an additional polymeric material cross-linked to the polymeric material. In some embodiments, the material comprises polyacrylamide, polyethylene glycol (PEG), poly (acrylate-co-acrylic acid) (PAA) or Poly(N-isopropylacrylamide) (NIPAM). In some embodiments, the synthetic 3D matrix is configured to expand.

In some embodiments, the cell or cell derivative is cleared of proteins, lipids, or proteins and lipids. In some embodiments, the method further comprises processing or modifying precursors of the plurality of nucleic acid molecules to facilitate interaction of the precursors with the synthetic 3D matrix. In some embodiments, the processing or modification comprises alkylation, oxymercuration, periodate oxidation of RNA 3' vicinal diols, carbodiimide activation of RNA and DNA 5' phosphate, psoralen and phenyl azide for functional attachment of acryloyl or click-reactive moieties.

In some embodiments, the method further comprises, prior to (a), providing a plurality of precursor nucleic acid molecules, and subjecting the plurality of precursor nucleic acid molecules to nucleic acid amplification to generate the plurality of nucleic acid molecules. In some embodiments, the plurality of precursor nucleic acid molecules is ribonucleic acid molecules, and wherein the nucleic acid amplification is reverse-transcription polymerase chain reaction (RT-PCR). In some embodiments, the plurality of precursor nucleic acid molecules is deoxyribonucleic acid molecules, and wherein the nucleic acid amplification is polymerase chain reaction (PCR). In some embodiments, the nucleic acid amplification is rolling circle amplification. In some embodiments, the plurality of nucleic acid molecules is ribonucleic acid molecules. In some embodiments, the plurality of nucleic acid molecules is deoxyribonucleic acid molecules. In some embodiments. (d) comprises sequencing each of the at least the subset of the plurality of nucleic acid molecules or derivatives thereof to generate sequencing reads. In some embodiments, the method further comprises processing the sequencing reads to identify one or more genetic aberrations in at least a subset of the plurality of nucleic acid molecules. In some embodiments, the one or more genetic aberrations are selected from the group consisting of copy number variation, single nucleotide variation, and insertion or deletion. In some embodiments, two or more nucleic acid molecules having the one or more genetic aberrations comprise the same index sequence.

In another aspect, the present disclosure provides a method for processing or analyzing a plurality of nucleic acid molecules of a cell or cell derivative, comprising: (a) obtaining a 3D spatial position of each of at least a subset of the plurality of nucleic acid molecules in a synthetic 3D matrix, wherein the plurality of nucleic acid molecules have a relative 3D spatial relationship: (b) separately from (a), identifying a sequence of each of the at least the subset of the plurality of nucleic acid molecules or derivatives thereof;

and (c) associating the 3D spatial position from (a) with the sequence from (b). In some embodiments, in (b), the sequence is identified by sequencing each of the at least the subset of the plurality of nucleic acid molecules or derivatives thereof. In some embodiments, the sequencing is massively parallel array sequencing. In some embodiments, the sequencing is sequencing by synthesis.

In another aspect, the present disclosure provides a system for processing or analyzing a plurality of nucleic acid molecules of a cell or cell derivative, comprising: (a) a database comprising (i) 3D spatial data indicative of a 3D spatial position of each of at least a subset of the plurality of nucleic acid molecules in a synthetic 3D matrix, wherein the plurality of nucleic acid molecules have a relative 3D spatial relationship, and (ii) sequencing data comprising a sequence of each of the at least the subset of the plurality of nucleic acid molecules or derivatives thereof; and (b) one or more computer processors coupled to the database, wherein the one or more computer processors are programmed to (i) retrieve the 3D spatial data and the sequencing data from the database, and (ii) associate the 3D spatial position with the sequence. In some embodiments, the system further comprises an electronic display comprising a graphical user interface configured to display a report associating the 3D spatial position with the sequence. In some embodiments, the one or more computer processors are programmed to generate an electronic report associating the 3D spatial position with the sequence. In some embodiments, the one or more computer processors are programmed to transmit the report to a user. In some embodiments, the one or more computer processors are programmed to transmit the report to a user over a network.

In another aspect, the present disclosure provides a method for processing or analyzing a plurality of nucleic acid molecules of a cell or cell derivative, comprising (i) determining a three-dimensional (3D) spatial position of each of at least a subset of the plurality of nucleic acid molecules in the cell or cell derivative, and (ii) with the at least the subset of the plurality of nucleic acid molecules or derivatives thereof removed from the cell or the cell derivative, identifying sequences of the at least the subset of the plurality of nucleic acid molecules or derivatives thereof. In some embodiments, the sequences are identified by sequencing.

In another aspect, the present disclosure provides a method for processing or analyzing a plurality of nucleic acid molecules of a cell or cell derivative, comprising (i) determining a three-dimensional (3D) spatial position of each of at least a subset of the plurality of nucleic acid molecules in the cell or cell derivative, and (ii) sequencing the at least the subset of the plurality of nucleic acid molecules or derivatives thereof to identify a sequence of each of the at least the subset of the plurality of nucleic acid molecules or derivatives thereof.

In another aspect, the present disclosure provides a method for processing or analyzing a plurality of nucleic acid molecules of a cell or cell derivative, comprising (i) subjecting the plurality of nucleic acid molecules to sequence identification to identify sequences of the plurality of nucleic acid molecules, and (ii) associating the sequences with one or more three-dimensional (3D) spatial positons within the cell or cell derivative from which the plurality of nucleic acid molecules were derived. In some embodiments, the sequence identification comprises sequencing.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
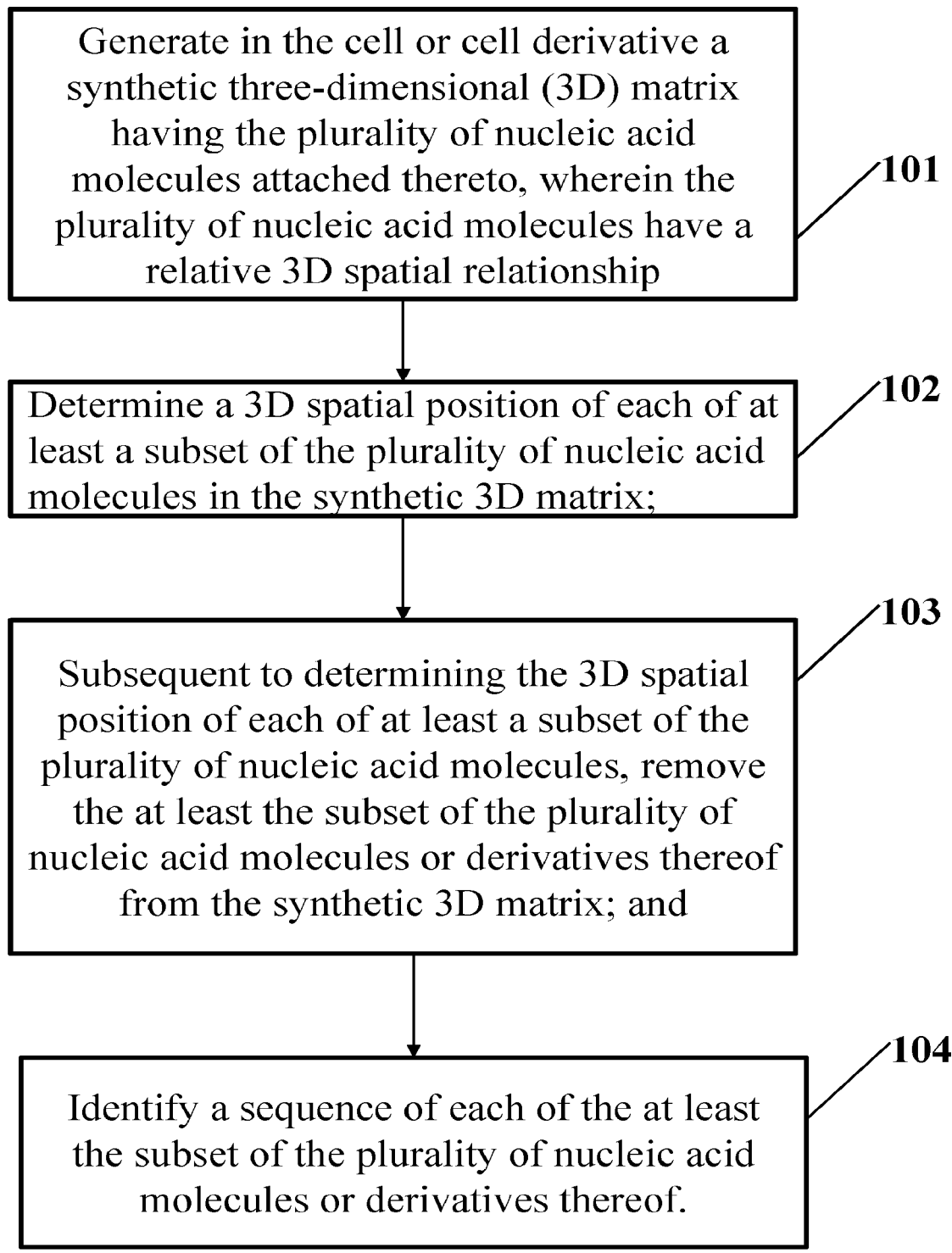
FIG. 1 shows a schematic of an example method for analyzing nucleic acids.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an" or "the" includes plural references unless the context clearly dictates otherwise. For example, the term "a cell" includes a plurality of cells, including mixtures thereof.

The terms "amplifying" and "amplification" generally refer to generating one or more copies (or "amplified product" or "amplification product") of a nucleic acid. The one or more copies may be generated by nucleic acid extension. Such extension may be a single round of extension or multiple rounds of extension. The amplified product may be generated by polymerase chain reaction (PCR).

The term "reverse transcription," as used herein, generally refers to the generation of deoxyribonucleic acid (DNA) from a ribonucleic acid (RNA) template via the action of a reverse transcriptase. The DNA may be a complementary DNA (cDNA). Such DNA may be hybridized to the RNA template. Reverse transcription PCR (or RT-PCR) refers to reverse transcription coupled with PCR.

The term "nucleic acid," as used herein, generally refers to a nucleic acid molecule comprising a plurality of nucleotides or nucleotide analogs. A nucleic acid may be a polymeric form of nucleotides. A nucleic acid may comprise deoxyribonucleotides and/or ribonucleotides, or analogs thereof. A nucleic acid may be an oligonucleotide or a polynucleotide. Nucleic acids may have any three dimensional structure and may perform various functions. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation, with a functional moiety for immobilization.

The term "spatial index," as used herein, generally refers to a nucleic acid that is used to identify the spatial origin of a target nucleic acid. A spatial index may comprise a specific sequence that can be indicative of particular location or spatial origin of the target nucleic acid. The volume or area related to a spatial index may be as small as to encompass the space of a single molecule, or as large as to encompass multiple small molecules or cells.

The term "solid state," as used herein, generally refers to a molecule that is covalently or non-covalently linked to a matrix, such as a three-dimensional (3D) matrix. The 3D matrix may be polymeric matrix. The 3D matrix may be a hydrogel. The term "effectively solid state" generally refers to a molecule that is confined to an area adjacent to the matrix and does not diffuse on the order of a timescale sufficient to perform an enzymatic or chemical reaction.

The term "rolony," as used herein, generally refers to a rolling circle colony, such as, for example, a colony of nucleic acid molecules generated by rolling circle amplification (RCA).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Fluorescent In Situ Sequencing Methods

Fluorescent in situ sequencing (FISSEQ) may be used to determine or infer the identity of endogenous or exogenous nucleic acid sequences, which may informationally representing the totality of molecular identities found in biological specimens, including endogenous RNA and DNA species, as well as proteins and other non-nucleic acid biomolecules. The molecular identities can be informationally converted into nucleic acid sequences, such as by associating a nucleic acid barcode (e.g., DNA barcode) with the molecule in the process of library construction. However, in some cases, FISSEQ may have some limitations, such as read length limitation and read speed. Methods and systems provided herein can overcome these limitations. In some cases, the methods and systems can overcome read-length limitations of fluorescent sequencing chemistries.

Fluorescent sequencing and next-generation sequencing chemistries may utilize a short or fragment sequencing read, wherein only part of the sequence of the original molecule or sequencing template can be detected. The length of sequencing reads generated by fluorescent sequencing chemistries can be within a range of 1-1000 nucleotides, or less than about 250) nucleotides in some cases. For example, the length of sequencing reads generated by fluorescent sequencing chemistries can be less than or equal to about 1000, 900, 800, 700, 600, 500, 400, 300, 200, or 100 nucleotides long. Therefore, in the case of the genome, of which each chromosome comprises tens or hundreds of millions of base pairs, it may not be feasible to generate correspondingly long sequencing reads using existing fluorescent sequencing chemistries. In the case of RNA molecular detection, endogenous RNA species can vary in length from the order of single nucleotides up to more than tens of thousands of nucleotides: in the latter case, it may also not be feasible to generate a correspondingly long sequencing read using existing fluorescent sequencing chemistries. Existing fluorescent sequencing chemistries can be used to generate relatively "short" or "fragment" sequencing reads, as compared to the original molecules. Longer sequences can be determined by use of a physically or computationally assembled "contig," or assembly of short reads into a longer contiguous sequence. For the purpose of sequence assembly, a number of sequencing approaches may be used to augment the sequence data from which sequences longer than the reads themselves are assembled. For example, de novo genomic and transcriptomic sequencing assays can utilize both more than one sequencing approaches, and/or algorithmic approaches of sequence assembly from short reads.

FISSEQ, using fluorescent sequencing chemistries, may share this fundamental limitation. Therefore, using traditional FISSEQ the sequencing read can be understood to serve the purpose of providing enough information for molecular detection or inference, or for detection of short sequence variations, wherein the target RNA or DNA species can comprise additional sequence, which is not detected or read out during FISSEQ. The additional sequence may be detected or sequenced later using a method other than FISSEQ.

The time and cost of a fluorescent sequencing assay can scale in relation to the length of the sequencing read. Because the nucleotide or another aspect of nucleotide sequence identity, such as dinucleotides, can be detected in a series of interleaved biochemical reactions and imaging steps, increasing the length of a sequencing read using fluorescence sequencing chemistries may need additional cycles, which in turn may need additional time and sequencing reagents.

In the case where a scientific instrument, such as a microscope, fluidic microscope, or automated sequencer are used to collect the sequencing data, increasing assay time per sample can cause a decrease in throughput for the number of samples which may be assayed. Since the cost of the instrumentation can be amortized over a number of samples assayed within a finite period of time, such as a period of several years, increased assay time may also thereby increase assay cost.

A sample described in the present disclosure can be a biological sample. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. A biological sample may be a cell-free sample. Such cell-free sample may include DNA and/or RNA.

In some cases, the methods and systems disclosed herein improve the accuracy of the sequencing.

In some cases, FISSEQ can be used for detection of nucleic acid barcodes, which can be indicative of a molecular species. In such cases, the barcode sequence may be designed to optimize the sequencing protocol for properties such as compactness and error robustness, e.g., by using barcode sequences of the minimum length for unique specification of each target species, or by adding error correction features to the barcode, such as redundant or parity bits of information.

In some cases, FISSEQ can be used for detection of endogenous nucleic acid sequences, such as RNA (e.g., mRNA, snRNA, microRNA, circRNA, etc.) and DNA (e.g., genomic DNA). In such cases, as few cycles of detection may be used, i.e., as short a sequencing read, as necessary for the purpose of molecular identification or inference can be performed. Therefore the detection of the endogenous sequence may, but in many cases may not, represent the most informationally compact or robust representation of molecular identity. For example, the requisite number of bases for disambiguation of two or more RNA species, while dependent on the molecular species, organism, etc., can be greater than the number of bases needed to uniquely identify two synthetic barcodes, which may be specifically associated through library construction with aforementioned two or more RNA species.

Moreover, for the purpose of sequencing accuracy, it can be common to re-sequence single molecules or the amplified derivative sequencing templates of single molecules, in series or in parallel. Single reads may contain errors, whereas ensemble sequences can be determined with greater precision. Using this additional data, in combination with computational models of the sequencing assay, it may be possible to infer the source of measured sequence variation as occurring during sequencing, library construction, or representing variation within the original sample.

However, in the case of traditional FISSEQ, the spatial origin of the fluorescence sequencing signals can represent the original position of the target molecules in the assay, either as an absolute position within a sample or as a position relative to other aspects or measurements taken of the sample. The spatial fidelity, and thereby the spatial information content, of FISSEQ sequencing data can be derived from the FISSEQ matrix, which can stabilize and provide for spatial invariance, as absolute or relative positional invariance or topological invariance, throughout the assay. However, in most cases, as a byproduct of this feature of the FISSEQ method, target molecules can be detected within the sample once, by sequencing the template co-located with the original target molecule. In some cases, FISSEQ can preclude the generation of multiple clonal sequencing templates for co-detection in parallel, as in next-generation sequencing. It may be possible to re-sequence the FISSEQ template or a derivative thereof in situ and/or in series at the cost of increased assay time and cost.

In some cases, the methods and systems disclosed herein may improve sensitivity. Because FISSEQ can utilize fluorescence signals in situ for molecular detection, the spatial density of sequencing templates, which may be resolved from each other, can be limited by the physical property of light known as the diffraction limit. Under common implementations of fluorescence microscopy, this can limit the resolution of detection to the order of hundreds of nanometers. However, the density of biomolecules within biological specimens may greatly exceed this limit. Therefore, without incorporating an approach for detection beyond this limit, the sensitivity of the FISSEQ assay may be limited on a per-molecule spatial basis.

Several methods can be used to enable the resolution of multiple objects within the limit. For example, super-resolution imaging can be used, including stimulated emission depletion (STED), stochastic optical reconstruction microscopy (STORM), photo activated localization microscopy (PALM), DNA-points accumulation for imaging in nanoscale topography (DNA-PAINT), expansion microscopy (ExM), and the like. In some cases, the super-resolution imaging methods may be highly specialized, which may need trade-offs with standard imaging in the cost and complexity of the imaging apparatus or assay. In some cases, the super-resolution imaging methods may need an increase in imaging time for data acquisition.

The super-resolution FISSEQ, also known as partition sequencing, can be used to enable the resolution of multiple objects within the limit. Partition sequencing can use a series of sequencing assays to determine the identity of multiple templates within the same resolution-limited volume, wherein the set of sequencing reactions within each assay can be directed to a subset of sequencing templates. In some cases, this approach can incur the cost of increased assay time, cost, and complexity.

Furthermore, limitations other than the diffraction limit of light may impede molecular detection with high sensitivity. For example, in the case where the FISSEQ library utilizes amplified sequencing templates (which are molecules occupying physical space), physical limitations such as steric, chemical, electrostatic, and other physical limitations may occur, preventing an arbitrary number of molecular detection events from occurring within the limited space.

The process of library construction may constrain the spatial density of the assay. For example, chemical or biochemical processes which consume one or more substrates may be limited by the availability of the substrate(s) given a reaction volume and kinetics. For example, tethering moieties within the 3D FISSEQ matrix may have limited availability for molecular tethering. For another example, PCR primers or nucleotides in polony or rolony gel constructions may have limited availability for amplification reactions to occur.

Finally, the efficiency of FISSEQ library construction may limit the sensitivity of the assay. FISSEQ library construction, as a relatively new and constrained instance of next-generation sequencing, may contain steps which are less efficient on a per-molecule basis than traditional next-generation sequencing or other sequencing technologies. Moreover, FISSEQ processes may be further limited in efficiency by the in situ nature of the biochemical steps.

Spatial Molecule Index (SMI) Enables Hybrid In Situ-In Vitro Detection

Molecular indexing can be a robust solution to a number of nucleic acid detection problems, as it can enable the physical or informational isolation of nucleic acids by one or more features, which comprise the indices. For example, the sequence specificity of restriction endonuclease reactions can be used to separate and analyze mixtures of nucleic acids. The practice of molecular indexing can be separated into the practices of in vitro and spatial indexing. The indices of in vitro indexing can be characterized by their utility in tracking, separating, and distinguishing nucleic acids from one another, whereas the indices of spatial indexing practices can be characterized by their utility in localizing the spatial origin of nucleic acids from a biological specimen. Although conceptually distinct, the practices may be combined in assay design.

Both of these indexing methods may be in contrast to inherently spatial molecular detection approaches, such as FISSEQ, wherein the molecular assay can be conducted in situ, within the assayed specimens, preserving the spatial organization of the target molecules and enabling simultaneous identification of the assayed molecular information and spatial position. Additional sequencing data generated in situ from the same template may be associated with the original data purely by virtue of the spatial position and other conditions of the sequencing reaction, such as sequencing primer or partition, and the relative or absolute spatial invariance of sequencing templates within FISSEQ samples.

In some cases, the SMI described herein can be a sample index. In some cases, the SMI described herein can be a molecular index such as UMI.

In Vitro Indexing

Two modern uses of in vitro indexing, which may be employed separately or together in assay design, can be to index collections of nucleic acids, referred to as sample indexing, and to index single nucleic acids, commonly referred to as unique molecular indices (UMI). For example, a sample index can be used to barcode each and every target nucleic acid from a single cell, a single sample comprising one or more cells, a single piece of tissue. For another example, a sample index can be used to barcode each and every target nucleic acid from a biological particle (e.g., a cell, an exosome, a nuclei, or the like). For another example, a UMI can be used to barcode a single target nucleic acid molecule within a cell, a tissue, or a sample comprising one or more cells, and each nucleic acid molecule can have a different (or unique) index sequence.

These indices may be contiguous with, embedded within, or entirely separate from the sequencing template. For example, using the Illumina platform, indices can be embedded within an adapter sequence and sequenced as a separate "index read" in a reaction primed from a separate sequencing primer. After the nucleic acids are indexed, subsequent reactions may be conducted on the pooled material, given subsequent reactions preserve the association between the index and the template molecules.

Sample Indexing

Due to the rapid increase in the throughput of next-generation sequencing technologies, it may be possible to sequence multiple samples in parallel. Using various library construction protocols, sample-specific index sequences (also called "barcodes") can be attached to the sample molecules during sequencing library preparation. Subsequently, the multiple libraries can be pooled and sequenced in a multiplex, parallelized reaction, and later computationally separated based on the index sequence.

Recent advancements may have scaled the sample input size for sequencing down to single cells. Numerous multiplexing approaches exist for associating unique barcodes with the nucleic acid content of individual cells. Early multiplexing approaches for RNA-sequencing may need sorting single cells into individual wells, wherein an index can be associated with the nucleic acids, such as during reverse transcription (RT), second strand synthesis, polymerase chain reaction (PCR), or in vitro transcription (IVT). Later multiplexing approaches may separate cells into droplets or picoliter wells, each corresponding to a single index.

Increases in the number of indices may need improvements in the methods used to generate large, diverse libraries of indices. In some approaches, the length of the index can be increased to increase the diversity of the index pool, while in other approaches, multiple shorter indices can be combined into a longer effective index. Longer indices may be built up from shorter indices, such as by using polymerase or ligase reactions, sometimes together with split-pool (also called mix and expand) approaches. These combinatorial barcoding approaches can be repeated to create arbitrarily complex pools of indices, resulting in an arbitrarily low probability of index collision, wherein two separate samples can come to bear an identical index by chance.

Unique Molecular Indices (UMI)

Many sequencing methods may rely on one or more amplification steps, such as to increase the amount or concentration of nucleic acid material. However, these amplification processes may introduce biases, which cause certain sequences to be over-represented in the final library relative to the initial abundance.

Unique molecular indices (UMIs: also called Random Molecular Tags, RMTs) can serve as single-molecule indices, which can index each molecule prior to amplification, enabling identification of clonal or duplicate molecules, and subsequent computational collapse of redundant data or computational analysis and correction of amplification or sequencing errors.

UMIs can be useful for low-input RNA-sequencing applications, such as single-cell RNA-seq, wherein the original molecules may vary greatly in abundance and significant amplification may be needed for detection.

Spatial Indexing

Spatial indexing can enable localizing the spatial origin of nucleic acids from a biological sample (e.g., a biological specimen) during a non-spatial assay, such as next-generation sequencing. Non-spatial assays, such as PCR, sequencing, mass spectroscopy, and others, can enable powerfully sensitive and massively multiplex assays of biomolecules, with the caveat that the spatial information associated with the origin of the assayed molecules may be lost during the assay process. Therefore, methods can be developed to provide spatial indices cognate to the target molecule, such as a sequencing template.

Spatial indexing can utilize sample indexing, with the additional step of tracking the association between the spatial origin of the sample and the index. For example, microdissection and laser capture methods can enable a region of interest (ROI) within a sample to be isolated from other aspects of the sample, enabling a known barcode to be associated with the sample. Subsequently, the origin of detected molecules may be determined using the index.

An example method can include planar (2D) capture by molecular barcode label liberation in user-specified regions of interest using the Nanostring Digital Spatial Profiling method. According to this method, molecular probes such as DNA-barcoded antibodies and in situ hybridization (ISH) probes can be applied to a sample, wherein the molecular index of the probe, i.e. the sequence of the probe used to identify the target molecule, can be liberated in a spatially-confined reaction, such as by cleaving a photo-labile linkage with a spatially-directed pattern of light: the liberated tags can be collected and associated with a spatial index, subsequently the molecular barcode and spatial indices can be detected, such as by using a multiplex, parallelized sequencing assay. The spatial indices can be used to separate the molecular barcodes, representing molecular detection events, by the corresponding region of interest. Another example method can include the application of spatially indexed oligonucleotide probes into user-specified ROIs for biomolecular capture. These ROI-based approaches may be limited in scalability, as each ROI may need to be spatially indexed in series (rather than parallel indexing).

In some cases, a method for spatial indexing can comprise applying a sample to a planar array of spatial indices, which may be associated locally with target molecules. For example, molecules inside cells and/or tissues can be captured onto a planar (2D) microarray. The planar microarray may comprise oligonucleotides attached thereto containing spatial indices. The oligonucleotides can be printed onto the planar microarray according to a known pattern. The sample can be permeabilized. Endogenous sequences from the sample can be tagged with the spatial index, such as by reverse transcription. According to another method, spatial index sequences can be seeded randomly onto a planar substrate. The spatial pattern of indices can be determined, for example, by sequencing. The spatial pattern of indices can be used to spatially tag endogenous molecules.

Rationale for Massively Parallel 3D Spatial Indexing

Biological specimens can be volumetric in nature (3D), with biologically and biomedically significant biomolecular processes spatially organized in all three dimensions. However, these existing methods of spatial indexing can be limited to planar (2D) spatial resolution. To achieve pseudo-3D resolution using 2D planar methods, it may be possible to physically section the biological specimen into arbitrarily thin sections, each of which is assayed in a planar manner. However, this approach can limit the scalability of the assay in terms of physical volume assayed, as increasing the resolution in the 3D dimension may need increasing the number of separate planar assay's.

Planar capture mechanisms, when used to spatially tag molecules originally organized within a 3D volume, may need transport of the endogenous molecules onto the planar surface to achieve spatial tagging: if the transport mechanism is diffusion, the 2D positional fidelity of the spatial indexing can become uncertain due to lateral diffusion enabling molecules originally located within one spatial index position to be captured by a separate spatial index position.

Therefore, methods for spatial indexing of biomolecules and biomolecular labels can be performed in a volumetric, or 3D, manner, improving the resolution of in situ spatial indexing for in vivo molecular detection, and which can enable parallel indexing of spatial regions within a specimen with arbitrary spatial multiplexity. Furthermore, by combining 3D spatial indexing with hydrogel and FISSEQ matrix expansion technologies, 3D spatial indexing may be achieved with arbitrary spatial resolution.

SMI Enables 3D In Situ Mapping of In Vitro Sequencing Data

Disclosed herein are methods, systems and compositions for determining the 3D spatial position and sequences of the nucleic acid molecules in a cell or cell derivative. The methods performed relate to 3D in situ indexing of nucleic acid molecules in a cell or cell derivative. 3D in situ spatial indexing can be achieved by constructing a synthetic 3D matrix which may comprise a 3D array of spatial indices, conferring the spatial indices to nucleic acid molecules, such as RNA, DNA, barcode tags and other nucleic acid biomolecular information-bearing constructions, and subsequently detecting the sequences of the spatial index and target molecule by sequencing in vitro. Sequences or a portion of sequences may also be detected using in situ sequencing techniques such as FISSEQ. Sequences or a portion of sequences may also be detected using probe molecules. In various methods described herein, sequencing reads obtained from in vitro and in situ sequencing may be processed in order to determine a 3D spatial position for a given molecule. The plurality of nucleic acid molecules can then be subjected to amplification reactions or can be released from the matrix. The nucleic acids and/or their derivatives can subsequently be collected and sequenced to identify a sequence of the nucleic acid molecules. These sequences can then be mapped or associated with their spatial index and a 3D spatial position can be identified based on information regarding the 3D spatial position of the spatial index.

An example embodiment of a method is demonstrated by FIG. 1. In operation 101, a 3D matrix can be generated in the cell or cell derivative. The synthetic three-dimensional (3D) matrix may have a plurality of nucleic acid molecules attached thereto. The plurality of nucleic acid molecules may have a relative 3D spatial relationship. Next, in operation 102, the 3D spatial position can be determined. Compositions and methods to generate the 3D matrix are provided in the present disclosure. Methods used to determine the 3D spatial position can comprise sequencing and/or hybridization. For example, the 3D spatial position can be determined by sequencing an index sequence co-localized with the target nucleic acid molecule. For another example, the 3D spatial position can be determined by hybridizing a probe having a detectable label attached thereto to an index sequence co-localized with the target nucleic acid molecule. The detectable label can then be detected to indicate the position of the target nucleic acid. Next, in operation 103, nucleic acids from the 3D matrix can be removed. Removal of the nucleic acid may comprise cleaving one or more linkages that attach the nucleic acid to the 3D matrix. Additional methods for removal are disclosed in the present disclosure. Next, in operation 104, a sequence of the nucleic acids can be identified. Methods of identifying the sequence may comprise sequencing (e.g., sequencing by synthesis) or hybridization (e.g., array hybridization). Identification by sequencing can comprise sequencing by synthesis, sequencing by ligation, or sequencing by hybridization. Identification by hybridization can comprise hybridizing a detection probe to the sequence to be identified.

Figure 2:
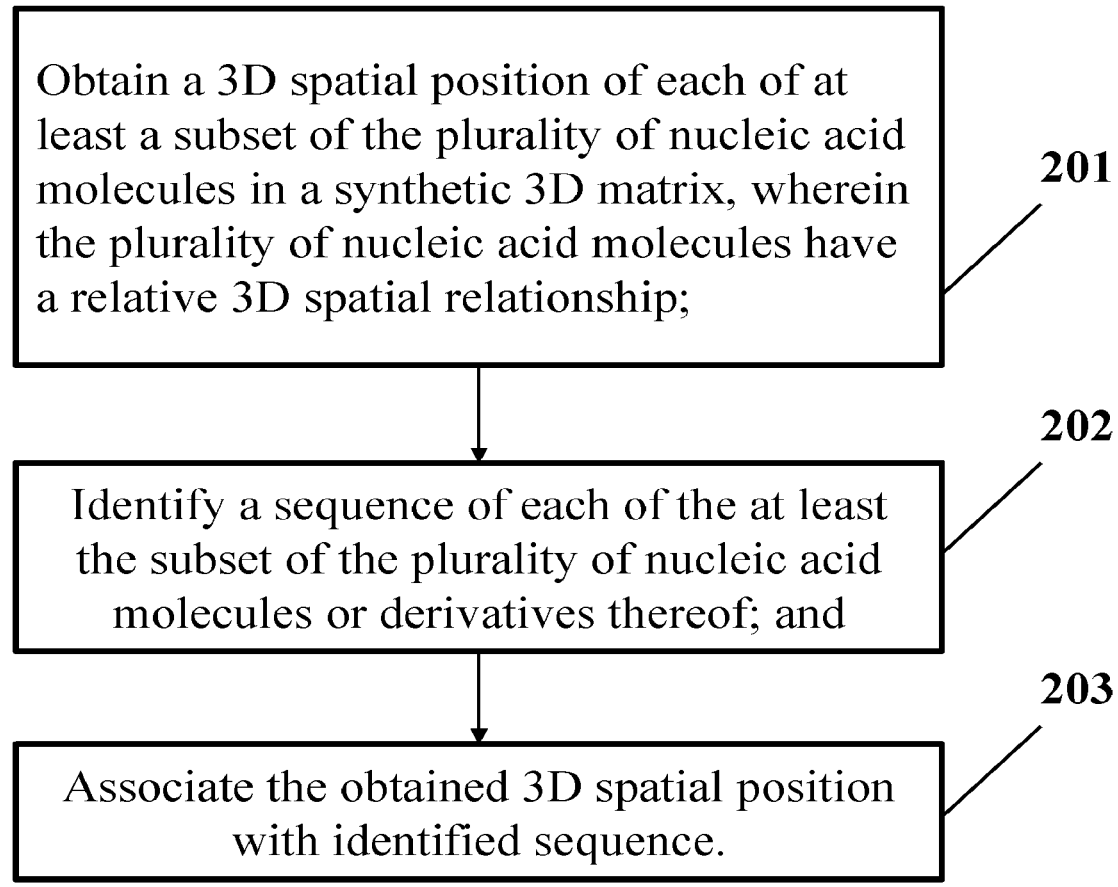
FIG. 2 shows a schematic of an example method for analyzing nucleic acids.

Another example of a method is demonstrated in FIG. 2. In operation 201, a 3D spatial position of each of at least a subset of the plurality of nucleic acid molecules in a synthetic 3D matrix is obtained. The plurality of nucleic acid molecules may have a relative 3D spatial relationship. Next, in operation 202, a sequence of each of the at least the plurality of nucleic acid molecules or derivative thereof can be identified. Next, in operation 203, the 3D spatial position and sequence of nucleic acids can then be associated. Association of the spatial position and related methods such as alignment or mapping may be performed by a computer processor.

For example, the 3D spatial position of each of the plurality of nucleic acid molecules in a synthetic 3D matrix is obtained. Next, the plurality of nucleic acid molecules is released or recovered from the 3D matrix (e.g., disrupting the 3D matrix) and used to generate a sequencing library. The sequencing library may be prepared by coupling adapters to the plurality of nucleic acid molecules. The adapters may be functional sequences, such as, for example, flow cell sequences (e.g., P5/P7 sequences) for use with a planar or flow-based sequencing platform (e.g., Illumina). The sequencing library may then be sequenced to generate sequencing reads, which may be analyzed with a computer and used to associate the sequencing reads with the 3D spatial positions of the plurality of nucleic acid molecules.

Construction of the 3D Spatial Indexing Matrix

3D Matrix Preparation

An in situ 3D matrix may be formed from an original biological specimen using a number of approaches described herein. Formation of the 3D matrix can cause the termination of in vivo biochemical processes, substantially preserving the biomolecules and their localization within the specimen. Common methods for forming the 3D matrix from a biological specimen can include fixation, or the formation of chemical or physical crosslinks among the 3D matrix of biomolecules, such as by temperature, electromagnetic radiation (e.g., microwave), or chemicals, such as formaldehyde, glutaraldehyde, or other material for biological sample fixation, within the cell and tissue. Any convenient fixation agent, or "fixative," may be used to fix the biological sample in the absence or in the presence of hydrogel subunits, for example, formaldehyde, paraformaldehyde, glutaraldehyde, acetone, ethanol, methanol, etc. In some cases, the fixative may be diluted in a buffer, e.g., saline, phosphate buffer (PB), phosphate buffered saline (PBS), citric acid buffer, potassium phosphate buffer, etc., usually at a concentration of about 1-10%, e.g. about 1%, 2%, 3%, 4%, 5%, 6%, 7%, 8%, or 10%, for example, 4% paraformaldehyde/0.1M phosphate buffer; 2% paraformaldehyde/0.2% picric acid/0.1M phosphate buffer: 4% paraformaldehyde/0.2% periodate/1.2% lysine in 0.1 M phosphate buffer: 4% paraformaldehyde/0.05% glutaraldehyde in phosphate buffer: etc. The type of fixative used and the duration of exposure to the fixative will depend on the sensitivity of the molecules of interest in the specimen to denaturation by the fixative, and may be readily determined using conventional histochemical or immunohistochemical techniques.

Additional non-limiting examples of fixatives include methanol, ethanol, acetone, paraformaldehyde, formalin and osmium tetroxide.

Alternatively, or in addition to the process of fixation, a tissue-chemical hydrogel may be formed by generation of chemical or physical crosslinks between biomolecules and other natural or synthetic components added to the sample to supplement or replace native cellular components for the purpose of immobilizing biomolecules. The chemical 3D matrix can comprise a polymeric compound. A 3D matrix may be formed in situ throughout the cell and tissue sample, such as through the formation of a hydrogel matrix. A hydrogel matrix may be formed upon cross-linking, gelling, or polymerizing subunits, such as, for example, cross-linking, gelling or polymerizing a polyacrylamide or polyethylene glycol (PEG). The 3D matrix may be generated by directing precursors of the 3D matrix in to the biological specimen and subjecting the precursors to crosslinking or polymerization reactions. For example, acrylamide may be directed into the biological specimen and polymerized to form polyacrylamide. Further according to this embodiment, the chemical matrix can be composed substantially of polyacrylamide. According to another embodiment, the 3D matrix can be an expanding FISSEQ matrix, such as one comprised substantially of poly(acrylate-co-acrylic acid) (PAA) or Poly(N-isopropylacrylamide) (NIPAM). The matrix comprising NIPAM may be expandable or configured to expand by a change in temperature. According to another embodiment, the 3D matrix can be composed substantially of cross-linked poly-ethylene-glycol (PEG). The PEG can be of various molecular weights.

The 3D matrix may be formed by various processes such as via free-radical polymerization, chemical conjugation and bioconjugation reactions. For example, the reaction between a primary amine and N-hydroxysuccinimide esters or between thiols and maleimides or other chemical mechanisms may be used to form the 3D matrix. Aggregation and non-covalent mechanism may also be used to generate the 3D matrix.

The 3D matrix may be formed using a photopolymerization. Photopolymerization may us photons to initiate a polymerization reaction. The photopolymerization reaction may be initiated by a single-photon or a multiphoton excitation system as described elsewhere herein. Light may be manipulated such to form specific 2D or 3D patterns and be used to initiate the photopolymerization reaction. This may be used to construct a particular shape or pattern for the 3D matrix such that the matrix is generated in one part of the cell or cell derivative but not generated in another part of the cell or cell derivative. Light and patterns of light may be generated by spatial light modulators, such as a digital spatial light modulator. The spatial light modulators may employ a transmissive liquid crystal, reflective liquid crystal on silicon (LCOS), digital light processing, a digital micromirror device (DMD), or a combination thereof.

The fixative/hydrogel composition may comprise any hydrogel subunits, such as, but not limited to, poly (ethylene glycol) and derivatives thereof (e.g., PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly (hydroxyethyl acrylate), and poly (hydroxyethyl methacrylate), collagen, hyaluronic acid, chitosan, dextran, agarose, gelatin, alginate, protein polymers, methylcellulose and the like. Agents such as hydrophilic nanoparticles, e.g., poly-lactic acid (PLA), poly-glycolic acid (PLG), poly(lactic-co-glycolic acid) (PLGA), polystyrene, poly (dimethylsiloxane) (PDMS), etc. may be used to improve the permeability of the hydrogel while maintaining patternability. Materials such as block copolymers of PEG, degradable PEO, poly(lactic acid) (PLA), and other similar materials can be used to add specific properties to the hydrogel. Crosslinkers (e.g., bisacrylamide, diazirine, etc.) and initiators (e.g., azobisisobutyronitrile (AIBN), riboflavin, L-arginine, etc.) may be included to promote covalent bonding between interacting macromolecules in later polymerization steps.

The nucleic acids (e.g., RNA molecule, cDNA molecule, primer, or probe) described herein may comprise a functional moiety. The nucleic acids can be linked to the 3D matrix by the functional moiety. The functional moiety can be reacted with a reactive group on the 3D matrix through conjugation chemistry. In some cases, the functional moiety can be attached to target of interest through conjugation chemistry. In some cases, the functional moiety can be directly attached to a reactive group on the native nucleic acid molecule. In some cases, the functional moiety can be indirectly linked to a target through an intermediate chemical or group. The conjugation approaches described herein are not limited to nucleic acid targets and can be used for protein or small molecule targets as well. A nucleotide analog comprising a functional moiety may be incorporated into a growing chain of the nucleic acid (e.g., cDNA molecule, probe, or primer) during nucleic acid synthesis or an extension reaction.

As used herein, the term "reactive group" or "functional moiety" generally refers to any moiety on a first reactant that is capable of reacting chemically with another functional moiety or reactive group on a second reactant to form a covalent or ionic linkage. "Reactive group" and "functional moiety" may be used interchangeably. For example, a reactive group of the monomer or polymer of the matrix-forming material can react chemically with a functional moiety (or another reactive group) on the substrate of interest or the target to form a covalent or ionic linkage. The substrate of interest or the target may then be immobilized to the matrix via the linkage formed by the reactive group and the functional moiety. Examples of suitable reactive groups or functional moieties include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

Further according to these aspects of the present disclosure, endogenous or exogenous biomolecules, especially nucleic acids, may be covalently or noncovalently linked to the 3D matrix, preserving the spatial origin of the molecules during sample processing. The nucleic acid molecules or derivatives thereof can be coupled to the 3D matrix by coupling agents. To facilitate coupling or other downstream processes, endogenous nucleic acids may be modified using chemical reactions, such as alkylation, oxymercuration, periodate oxidation of RNA 3' vicinal diols, carbodiimide activation of RNA and DNA 5' phosphate, or by other nucleic-acid reactive chemistries such as psoralen and phenyl azide, for functional attachment of acryloyl or click-reactive moieties, which may be subsequently reacted with the 3D matrix. Alternatively, endogenous nucleic acids may be modified using biochemical reactions, such as ligation, polymerase extension, and hybridization, for functional attachment of acryloyl or click-reactive moieties, which may be subsequently reacted with the 3D matrix. For example, a DNA molecule may be ligated using a DNA ligase to attach the 3D matrix to the DNA molecule. The coupling reaction may couple sequences comprising an index to the 3D matrix, or may couple sequences to the 3D matrix that may be subsequently indexed or subjected to another reaction as described elsewhere herein.

Reference to the 3D matrix should be understood to be inclusive of a number of matrix compositions, including those comprised of biomolecules, synthetic polymers, hydrogels, or combinations thereof. An intermediate or final 3D matrix composition may comprise multiple independently formed matrixes, such as re-embedded hydrogels, or other forms of spatially coincident, or in situ, 3D matrix(es).

Further according to these aspects of the present disclosure, the synthetic 3D matrix may be partially or substantially cleared of certain species or classes of biomolecules, such as lipids and proteins, as by use of detergent and/or protease reagents. According to some aspects of the present disclosure, the sample can be cleared using a detergent solution, such as Triton-X or SDS. The detergent may interact with the molecules allowing the molecules to be washed out or removed. Other non-limiting examples of detergents include Triton X-100, Triton X-114, Tween-20, Tween 80, saponin, CHAPS, and NP-40. According to some aspects of the present disclosure, the sample can be cleared using a protease reaction, such as Proteinase K. The protease may cleave or digest proteins such that the fragments or amino acids can be removed. According to some aspects of the present disclosure, the extracellular matrix can be substantially cleared using one or more specific or non-specific proteases. Other non-limiting examples of protease include trypsin, chemotrypsin, papain, thrombin, and pepsin.

The synthetic 3D matrix may be immobilized onto a solid substrate, such as glass or plastic, facilitating handling and reagent exchange. According to one aspect, the 3D matrix can be affixed to a glass slide via oxysilane-functionalization with acrylamide- or free-radical-polymerizing groups, such as methacryloxypropyltrimethoxysilane. The 3D matrix may be free-floating or otherwise not attached to a solid substrate.

A matrix may be used in conjunction with a solid support. For example the matrix can be polymerized in such a way that one surface of the matrix is attached to a solid support (e.g., a glass surface, a flow cell, a glass slide, a well), while the other surface of the matrix is exposed or sandwiched between two solid supports. According to some aspects of the present disclosure, the matrix can be contained within a container. In some cases, the biological sample may be fixed or immobilized on a solid support.

Solid supports of the present disclosure may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

The term "solid surface" or "solid support," as used herein, refers to the surface of a solid support or substrate and includes any material that can serve as a solid or semi-solid foundation for attachment of a biological sample such as polynucleotides, amplicons, DNA balls, other nucleic acids and/or other polymers, including biopolymers. Examples of materials comprising solid surfaces include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Examples of plastics include acrylics, polystyrene, copolymers of styrene and other materials, polypropylene, polyethylene, poly butylene, polyurethanes and Teflon™. Examples of silica-based materials include silicon and various forms of modified silicon.

Solid surfaces can also be varied in their shape depending on the application in a method described herein. For example, a solid surface useful in the present disclosure can be planar, or contain regions which are concave or convex.

Spatial Molecular Properties of 3D Index Field

The collection or plurality of spatial indices used in an assay can be referred to as a "field", whereas references to one or more spatial index(es) (or indices) should be understood to represent the sequence identity of the index(es), regardless of the number of molecules comprising the index(es). For example, a particular spatial index may exist as a single molecule, or as a collection of spatially co-localized molecules, which can be clonal or substantially clonal in sequence, at the time of indexing.

According to an embodiment of the present disclosure, the field of spatial indices may be substantially structured, or organized in a regular pattern. According to another embodiment of the present disclosure, the field of spatial indices may be substantially unstructured, or random in organization.

According to an embodiment of the present disclosure, the field of spatial indices may be sparse, i.e. filling the volume corresponding to less than 100% of the original volume or relative volume of the biological specimen. For example, the field of spatial indices may fill a partial volume of the biological specimen such as an organelle or cell compartment (e.g., nucleus, mitochondria, rough endoplasmic reticulum, Golgi apparatus, cytoskeleton, smooth endoplasmic reticulum, lysosome, cell membrane, etc.). In such an example, the field of spatial indices may index for example, the mitochondria, but not the nucleus, to identify target molecules specific to the mitochondria. According to another embodiment, the field of spatial indices is dense, i.e., substantially filling the original volume or relative volume of the biological specimen. For example, the field of spatial indices may fill an entire cell for indexing.

According to one aspect, the field of spatial indices is substantially spatially clonal, meaning any particular unit of volume within the sample comprises one or fewer unique spatial indices. For example, a single molecule may be uniquely indexed by a single index. In some cases, the plurality of spatial indices within a cubic nanometer is a clonal population of a unique index. In some cases, a volume comprising a diameter from about 100 to 200 nanometers, from about 200 to 300 nanometers, from about 300 to 400 nanometers, from about 400 to 500 nanometers, from about 500 to 600 nanometers, or from about 600 to 700 nanometers, may be a clonal population of a unique index. The volume comprising a diameter greater than or equal to 700 nanometers may comprise clonal population of a unique index. The clonal population may be generated from a single index molecule. For example single index molecule may be amplified to create multiple index molecules. The amplification of a single index molecule may generate a polony or a rolony. According to a separate aspect, the field of spatial indices can be partially spatially clonal, wherein any particular unit of volume within the sample can comprise an arbitrary number of spatial indices. For example, a unit of volume comprising multiple molecules may interact randomly with multiple indices. Further according to one embodiment, the spatial distribution of spatial indices can be approximately Poisson, with an average density (number of molecules per unit of volume) of less than one, approximately one, approximately two, approximately three, approximately four, or more. According to another embodiment, the spatial distribution of spatial indices can be sub-Poisson, meaning the variance of the distribution is less than the mean, wherein the mean spatial distribution of spatial indices per unit volume can be less than one, approximately one, approximately two, approximately three, or approximately four, or more. According to a separate embodiment, the field of spatial indices can be substantially spatially polyclonal, or non-clonal, meaning any particular unit of volume within the sample comprises more than one spatial index.

The spatial density and distribution of spatial indices within the field may be controlled by using chemical or biochemical processes which consume one or more substrates, which may be titrated or modulated by changing the reaction volume and reaction kinetics. One such example can be the limited availability of tethering moieties within the 3D matrix available for molecular tethering. The limited availability of the tethering moieties may allow only a subset of indices to tether to the 3D matrix. The availability of coupling agents may control or change the spatial density and distribution of spatial indices. For example, the limited availability of PCR primers or nucleotides (which may act as a coupling agent) in polony or rolony gel constructions may be used to control the spatial distribution or density of spatial indices. In such an example, a subset of polonies/rolonies is subjected to an extension reaction, whereas another subset is not subjected to an extension reaction. In some cases, the concentration of coupling agents can be less than the concentration of the nucleic acid molecules that can be coupled. In some cases, the concentration of coupling agents can be more than the concentration of the nucleic acid molecules that can be coupled. In some cases, the concentration of coupling agents can be substantially similar to the concentration of the nucleic acid molecules that can be coupled. Another such example can be the kinetic exclusion amplification method used in Illumina flow cells, wherein the reaction can include simultaneously transporting the nucleic acids to sites at an average transport rate, and amplifying the nucleic acids that transport to the sites at an average amplification rate, wherein the average amplification rate can exceed the average transport rate.

In the case where any particular unit of volume is spatially non-clonal in index, it may be possible to obtain or track the spatial position of one or more spatial indices within the sample. This may be done to analyze the origin of assayed molecules bearing the index to be in the position of the known index. For example, in the case spatial indices are generated via in situ synthesis according to a known pattern, knowledge of the origin of each index can be preserved independently of the spatial clonality of the indices. In the case spatial indices are generated randomly or pseudo-randomly, and the spatial origin of each index can be determined via fluorescent in situ sequencing (FISSEQ), the spatial origin of spatially non-clonal sequences may be determined using, for example, super-resolution microscopy and signal processing, including, but not limited to, the methods of partition FISSEQ and computational deconvolution of FISSEQ signals.

The plurality of indices may have a particular concentration. For example, the concentration of the plurality of indices may be less than or equal to about 100 molecules per cubic nanometer. The concentration of the plurality of indices may be less than or equal to about 900, 800, 700, 600, 500, 400, 300, 200, or 100 molecules per cubic nanometer. The concentration of the plurality of indices may be greater than or equal to about 200, 300, 400, 500, 600, 700, 800, 900 or more molecules per cubic nanometer.

SMI Spatial Resolution

The clonality can be relevant to indices as either single molecules or collections of substantially identical molecules, given an arbitrary unit of volume. Single molecules may occupy a finite, non-zero amount of space, but may be reasonably further generalized to a local area, in some cases on the scale of angstroms or nanometers, given the dynamics of molecular motion. Therefore, single molecule indices can be spatially clonal in the instance where the considered unit volume is at the corresponding size of single molecules.

According to one aspect of the present disclosure, the spatial indexing reaction can be confined to the regions occupied by the spatial indices. For example, the target molecules may be sufficiently proximal to spatial index molecules for effective indexing chemistry or biochemistry to proceed. The molecules of the target molecule and the index molecule can be considered to be solid state or effective solid state, wherein solid-state can refer to having a linkage to the 3D matrix, such as a covalent or noncovalent chemical linkage, and effectively solid-state can refer to the property of being otherwise substantially immobilized within the 3D matrix, such as by being topologically interconnected or being sterically confined from freely diffusing over timescales relevant to spatial indexing.

According to one aspect of the present disclosure, the spatial indexing reaction can be confined to the regions occupied by the spatial indexes. For example, target molecules can be sufficiently proximal to spatial index molecules for effective indexing chemistry or biochemistry to proceed, wherein the target molecule or the index molecule can be considered to be solid state or effective solid state. The target molecule or the index molecule as solid state can have a linkage to the 3D matrix, such as a covalent or noncovalent chemical linkage. The target molecule or the index molecule as effectively solid state can be substantially immobilized within the 3D matrix, such as by being topologically interconnected or being sterically confined from freely diffusing over timescales relevant to spatial indexing.

According to some embodiments, the spatial index and/or target molecules can be allowed to diffuse locally, in order to facilitate the indexing reaction or increase the efficiency of the indexing reaction on a per-molecule basis. For example, pre-existing linkages between the 3D matrix and either the target molecule or index molecule may be released, such as by breaking a chemical bond located within the 3D matrix, within the liberated molecule, or between the 3D matrix and the liberated molecule. For example, reactions used to couple the target molecule and the 3D matrix can be reversed. Example embodiments include by the reversal of formaldehyde cross links, by the proteinase and/or detergent clearing of a protein-lipid matrix to which molecules are fixed, reduction of a hydrogel matrix comprised of N,N'-Bis(acryloyl)cystamine (BAC), or by use of reversible linkage chemistries.

While these embodiments of the present disclosure may be considered to reduce the spatial resolution of indexing, the overall spatial resolution of indexing may be modulated using methods described herein, including but not limited to controlling the overall density and/or local density of indices within the spatial index field and index molecules within a spatial index, by the mass transfer properties of the 3D matrix, such as the pore size of a hydrogel matrix and effective coefficient of diffusion for relevant nucleic acid molecules, and by the efficiency of the indexing capture mechanism.

Amplification Methods

In some embodiments, target molecules and/or index molecules are subjected to amplification reactions. In some cases, the index may comprise a collection of spatially co-localized molecules, which are clonal or substantially clonal in sequence, the molecules comprising the index may be generated using amplification from a single template molecule, or by parallel synthesis techniques, wherein the molecules comprising the index can be synthesized separately but in a manner consistent with their function as a spatial index, i.e., with the index molecules comprising the same or substantially similar index information content.

Nucleic acid molecules, such as SMI molecules or endogenous molecules may be amplified using various methods for nucleic acid amplification, including solid-state or semi-solid-state amplification methods. Nucleic acid molecules can be amplified by rolling circle amplification (RCA), as by using a circular template molecule and an enzyme capable of rolling circle amplification, such as Phi29, Bst, Vent, 9°N DNA polymerases and related enzymes. Nucleic acid molecules can be amplified by polymerase chain reaction (PCR), as by using a DNA polymerase enzyme. Nucleic acid molecules can be amplified by an RNA polymerase using the in vitro transcription reaction, such as by T7 RNA polymerase. In some cases, nucleic acid molecules can be subjected to multiple different amplification reactions. For example, amplified RNA molecules can be subsequently converted to cDNA, such as by using a reverse transcription (RT) reaction. Conversion of RNA to cDNA may occur during any step of the indexing and subsequent library construction processes. Other methods of nucleic acid amplification include, but are not limited to, loop mediated isothermal amplification (LAMP), nucleic acid sequence based amplification (NASBA), self-sustained sequence replication (3SR), strand displacement amplification, and multiple displacement amplification. The resulting population of clonal, or substantially clonal indexing molecules is referred to as the amplicon.

The amplicon may comprise functional linkage groups for tethering to the 3D matrix, such as acrylamide or click-reactive groups, enabling the products of amplification to be spatially immobilized via covalent gel linkages. According to one aspect, the functional linkages can be incorporated during amplification using nucleotide analogs, including amino-allyl dUTP, 5-TCO-PEG4-dUTP, C8-Alkyne-dUTP, 5-Azidomethyl-dUTP, 5-Vinyl-dUTP. 5-Ethynyl dUTP, or a combination thereof. According to a separate aspect, for amplification methods using one or more primers, one or more of the primers may comprise a functional linkage group for tethering to the 3D matrix, i.e. solid-state. According to one embodiment, the spatial index field within the 3D matrix can comprise a polony gel.

Further, the amplicon may be subsequently processed, chemically or biochemically, using mechanisms including, but not limited to, fragmentation, end-modification, second-stranding, annealing of accessory strands, such as priming, gap filling, circularization, blunt ending, phosphorylation, dephosphorylation, protection, and deprotection. End-modifications may entail the addition and/or removal of bases or sequences. For example, additional sequences may be used to subject the amplicons to next generation sequencing reactions. End modifications may also entail adding chemical moieties that may be useful for linkages or coupling the amplicons to another molecule. For example, the end may be phosphorylated or dephosphorylated by an enzyme, for example, a kinase or phosphatase. Protecting group may also be added or removed to allow or prevent particular reactions from taking place. Blunt Ending may also occur in which an overhang comprising a portion of single stranded nucleic acid is removed. Amplicons may be subjected to second stranding reactions which may result in additional nucleic acid molecules. Second stranding may be performed by adding in a primer which is complementary to the amplicon and a polymerizing enzyme to generate additional nucleic acid molecules. Amplicons may also be subjected to gap filling via a polymerizing enzyme, which may link two strands of DNA together via the synthesis of intervene bases. Amplicons may also be circularized via the activity of a gap filling reaction, extension reaction, ligation reaction, or a combination thereof, in which a circular nucleic acid is generated from a linear nucleic acid.

The amplicon or subunits thereof may be processed into a greater plurality of subunits, such as by fragmentation. Methods of fragmenting the amplicon include mechanisms which are random, or substantially random, including by the DNA hydrolysis or DNA nicking activities of enzymes including, but not limited to, DNase, endonucleases, and DNA repair enzymes. According to one aspect of the random fragmentation mechanism, nucleotides or nucleotide analogs can be incorporated into the amplicon during synthesis, which subsequently become the site of amplicon fragmentation. Examples include incorporation of dUTP with fragmentation by Uracil-Specific Excision Reagents (USER), such as the combination of Uracil DNA Glycosylase (UDG) and an endonuclease such as Endonuclease VIII or Endonuclease IV: incorporation of inosine with fragmentation by Endonuclease V; and by incorporation of monomers bearing internal cleavage sites, such as oligonucleotides with internal disulfide or bridging phosphorothioate linkages during ligase-mediated amplification. Methods of fragmenting the amplicon can include mechanisms for site-directed fragmentation, such as by restriction endonucleases, for which single-stranded sites may be splinted with an accessory oligonucleotide to facilitate the restriction endonuclease reaction, and by other sequence-specific nucleic acid cutting mechanisms including by Cas9, C2c2, and other nucleic-acid-directed nucleic-acid restriction enzymes, and by Transcription Activator-Like Effector Nucleases (TALENs). According to some embodiments, a rolling circle amplicon can be fragmented into a plurality of indexing molecules. Fragmentation may also be performed by subjecting a rolling circle amplicon to a reverse primer in a process known as hyperbranched RCA. For example, RCA may create a long nucleic strand comprising multiple repeats of the template nucleic. Subjecting the amplicon to a reverse primer may allow a polymerization may create separate double strand DNA molecules resulting in the RCA amplicon being fragmented.

Sequence Properties of the Spatial Indices

The 3D spatial indices can comprise one or more nucleic acid sequence domains, which corresponds to the positional information of the index. Any sequence or collection of sequences may serve as a spatial molecular index, given the relationship between the spatial distribution of the indices and the sample is known, or at least partially known. The spatial index comprises one or more contiguous nucleotide sequences. A nucleotide sequence can comprise one or more bases. The spatial indices may be of a particular length. For example the spatial indices may be less than or equal to about 200, 150, 100, 90, 80, 70, 60, 50, 40, 35, 30, 20, 19, 18, 17, 16, 15, 14, 13, 12, 11, 10, 9, 8, 7, 6, 5, 4, 3, or 2 nucleotides long. Alternatively, the spatial indices may be greater than or equal to about 2, 3, 4, 5, 6, 7, 8, 9, 10, 11, 12, 13, 14, 15, 16, 17, 18, 19, 20, 25, 30, 35, 40, 50, 60, 70, 80, 90, 100, 150, 200 or more nucleotides long.

The spatial organization of the index field may be determined prior to, or subsequent to, generation of the field. If the spatial indices are synthesized in situ according to a predetermined pattern, the pattern may be stored for the purpose of mapping the measured indices into space. Alternatively, the spatial indices may be synthesized in situ or otherwise generated in such a manner that the organization is not predetermined, in a subsequent step the spatial organization of the index field may be determined by in situ sequencing (e.g., FISSEQ). The spatial indices may be both synthesized in situ according to a predetermined pattern, and also measured by in situ sequencing (e.g., FISSEQ), such as for the purpose of error detection and/or validation.

According to one aspect of the present disclosure, the SMI can be considered to be a unique index for each indexed spatial origin within the 3D matrix and corresponding specimen, enabling association of in vitro sequencing data with the spatial origin within the original sample. According to another aspect of the present disclosure, the SMI can be considered a substantially unique index for each indexed spatial origin within the 3D matrix and corresponding specimen. However, a sequence can be considered a SMI to the extent that it can be used to infer any spatial information about the origin of the detected molecule, i.e. conveying enough information to infer at least a non-uniform probability of origin among the field of indices.

In the cases where the SMI may not be considered to be a unique index for each spatial origin, additional non-SMI information may be used to support inference of the spatial origin of the target molecule. Sources of additional information include, but are not limited to, sequence variation, such as alternative splicing, SNP, expressed SNP, and spatial and biological context. Further according to this example, two identical SMIs can be used to index target RNA molecules or their derivatives, such as cDNA or in situ sequencing templates, and corresponding in vitro sequencing reads are generated, which can comprise both SMI sequences and template cDNA sequences. One SMI can be detected in situ within the nucleus of a cell, while the other can be detected within the cytoplasm of a cell. In the in vitro sequencing data, the cDNA segment of one read can be found to include intronic sequences indicative of a pre-spliced or precursor RNA molecule, while the other can be found to comprise entirely exonic sequences indicative of a fully spliced RNA molecule. Since splicing can occur predominantly in the nucleus, wherein cytoplasmic RNA molecules can be considered to be predominantly spliced, the SMI together with this additional spatial, biological, and sequence contextual information can enable inference of the unique spatial origins of each RNA molecule despite sharing identical SMI sequences. In another example, the additional information may take the form of sequence variation present in diseased cells, such as cancer mutations, wherein redundant SMIs can be found within both diseased and non-diseased cells.

Use of SMI in FISSEQ Sequencing Templates

According to certain embodiments of the present disclosure, the original spatial origin can refer specifically to a sequencing template within a FISSEQ library. Using FISSEQ, each sequencing template within the sequencing library can correspond to exactly one single original molecule, or part thereof, or molecular complex thereof (as in the case of proximity co-detection methods of library construction, such as proximity ligation), within the sample. The reverse may not be true, a single original molecule within the sample may generate any number of sequencing templates, such as in the case of genomic FISSEQ applications, where a number of sequencing templates can be generated from a single chromosome. However, according to certain embodiments of FISSEQ, each sequencing template can be detected once by in situ sequencing, and in the position of the original molecule.

In some embodiments of FISSEQ, the SMI can serve to localize the spatial origin of one or more in vitro sequencing data points with the spatial origin of the original FISSEQ sequencing template, which itself can be localized to the position of the original molecule, using in situ sequencing. Moreover, according to certain aspects, the SMI may serve the additional role of an Unique Molecular Index (UMI), as described herein. The two or more sequencing reads can be generated from a shared sequencing template: in each sequencing read, the SMI can be detected, in part or full. Each sequencing read may comprise additional sequence other than the SMI. According to a particular aspect of the present disclosure, at least one in vitro sequencing read can comprise additional nucleotide sequence of the original molecule relative to the in situ sequencing read.

According to certain methods of FISSEQ library construction, one or more nucleic acid molecules within a biological sample, which can be intended to be subjected to FISSEQ library construction, can be converted into a sequencing template, which can be subsequently detected via fluorescent sequencing chemistries. This process of library construction may involve one or more steps of modification, copying, and/or amplifying the original molecule, such as by using a variety of biochemical methods, including fragmentation, end processing, reverse transcription, second stranding, capture by circularization, end-ligation, polymerase chain reaction, rolling circle amplification, and all other methods encompassing forms of "message composition". Despite the diversity of library construction methods, there exist physical mechanisms for associating a SMI with the information present in the sequence of the original molecule, i.e., cognate to the original sequence or to a derivative sequence.

These mechanisms can fall broadly into three categories: use of endogenous sequence as SMI, use of exogenous sequence as SMI, and in situ generation of the SMI. The endogenous sequence used as the SMI sequence can present within the biological sample or specimen prior to library construction. The exogenous sequence used as the SMI sequence can be introduced en bloc during library construction.

According to the first mechanism, endogenous sequence can be used as SMI. For example, the short sequencing read itself may serve as an SMI, enabling mapping of the short in situ sequencing read to a longer in vitro sequencing read generated from a common sequencing template. Endogenous sequences may serve as an SMI due to the diversity of natural DNA and RNA sequences present within biological organisms, in which any particular short sub-sequence has a relatively small probability of occurring as multiple distinct sequencing templates within an in situ sequencing library by chance, and therefore can serve the purpose of discrimination among the reads between the two or more datasets. The diversity of sequences present in the in situ sequencing library may also be enhanced by the process of library construction, in which the SMI can comprise an endogenous sequence, but the proximity of the endogenous SMI sequence to biochemical library construction events, such as fragmentation sites, tagmentation, circularization, or to exogenous adapters introduced during library construction can serve to provide additional contextual information to the SMI sequence. For example, two genes of the same species, and comprising the same original sequence, may be detected separately, by virtue of having distinct SMI sequences, due to stochastic fragmentation of the original molecule occurring at non-identical sites during in situ library construction.

According to another mechanism, use of exogenous sequence as SMI, the FISSEQ sequencing read may comprise in part or whole a synthetic barcode serving as an SMI, which can be introduced en bloc during in situ library construction. For example, the degenerate random hexamer primer or a separate short degenerate sequence present on the 5' end of the reverse transcription primer may serve as an SMI. Exogenous SMI sequences may be introduced en bloc during library construction as degenerate sequences (e.g., synthesized as an equal or otherwise proportion of A, C, G, T, or in general of any two or more nucleobases), or by using a library of known sequences. The SMI sequences may be introduced within a probe construct, such as a padlock probe, molecular inversion probe, RT primer, second strand primer, etc., and be introduced by chemical and biochemical mechanisms, including by nucleic acid polymerization and/or ligation. In some cases, the probe construct may comprise a common sequence. The common sequence can later be used for further probing and/or sequencing. According to one aspect of the present disclosure, an enzyme bearing "cut and paste" functionality, such as a transposase, can be used to insert an SMI sequence into the sequencing template at a known position. Construction of the exogenous SMI, or collection of SMIs, may be guided by statistical concepts such as collision, e.g., as described by the "birthday problem", or to provide certain other desirable characteristics such as error robustness. For example, SMI collision (or the "birthday problem") is the event of observing two reads with the same sequence and same SMI barcode but originating from two different genomic molecules. SMI collision can be a function of the number of SMIs used, the number of unique alleles and the frequency of each allele in the population. In genome-wide sequencing experiments, the chance of SMI collision may be very low because the number of reads sharing the same sequence may be very small. In some other sequencing studies such as amplicon sequencing, a specific location in the genome is sequenced in many different cells, usually for the purpose of identifying or quantifying rare alleles. In this case, the sequencing depth can be much greater than genome-wide sequencing and many alleles from different genomic molecules can share the same sequence. Because of this, the possibility of SMI collisions can be much higher and may need to be taken into consideration in SMI design and analysis of sequenced reads.

According to the third mechanism, the SMI sequence can be generated in situ during in situ library construction. The SMI sequence may be generated using chemical or biochemical nucleic acid synthesis techniques, and can include mechanisms which are templated, un-templated, or partially templated. According to one embodiment, a terminal transferase can be used to add random, un-templated bases to the 3' end of a sequencing template molecule or precursor molecule. According to another embodiment, the SMI can be constructed via two or more reactions of a DNA polymerase or DNA ligase. Other mechanisms for constructing the index sequences in situ are described in the present disclosure.

According to some aspects of the present disclosure, the SMI can also be considered to be a unique index for each sequencing template within the in situ library, enabling association of multiple sequencing reads with a single template present in the original sample, which itself under certain embodiments corresponds to a single molecule within the original sample. According to another aspect of this embodiment of the present disclosure, the SMI can be considered a substantially unique index for each sequencing template within the in situ library. However, the SMI may be used for this purpose of linking in situ and in vitro sequencing data to the extent that when integrating two or more sequencing datasets, the sequence is capable of discriminating between at least two shared sequencing templates between the two datasets, i.e. conveying enough information within one dataset to eliminate at least one sequence as not sharing a sequencing template within the other dataset.

3D Spatial Indexing by In Situ Index Field Synthesis

Knowledge of the spatial pattern of indices may be achieved by directing the 3D synthesis of the index field in situ within the 3D matrix according to a predetermined pattern. The spatial indices may be organized in 3D space en bloc or indices may be built up from parts. Further, according to either aspect, the molecules comprising the index may be generated using amplification from a single template molecule, or by parallel synthesis techniques, wherein the molecules comprising the index can be synthesized separately but in a manner consistent with their function as a spatial index, i.e., with the index molecules comprising the same or substantially similar index information content. The synthesis may comprise templated nucleic acid synthesis, un-templated nucleic acid synthesis, or partially templated nucleic acid synthesis. The un-templated nucleic acid synthesis may comprise using an enzyme which randomly polymerizes nucleotides to the ends of the nucleic acid molecules. For example, a reverse transcriptase or polymerase may add random nucleotides to the end of nucleic acid molecules or amplicons. For example, the un-templated nucleic acid synthesis may comprise using a terminal transferase. A templated nucleic acid synthesis may incorporate steps that are un-templated which may increase the number of unique indices. The indices may be synthesized with polymerizing enzyme, a ligating enzyme, or both a polymerizing enzyme. For example, the polymerizing enzyme may be a deoxyribonucleic acid polymerase. For example, the ligation enzyme may be a deoxyribonucleic acid ligase. The indices may use a combination of enzymes. For example, a portion of the index may be synthesized via a polymerase and then ligated to another portion.

To achieve either a 3D localization of en bloc indices or in situ constructed indices, an aspect of immobilization chemistry may be needed to be localized in 3D space within the matrix. According to one aspect, the immobilization chemistry can be the formation of a linkage between the 3D matrix and an en bloc index molecule. According to a separate aspect, the immobilization chemistry can be the formation of the linkages, such as phosphodiester bonds formed within the backbone of a nucleic acid strand and hydrogen bonds formed by the base-pairing of complementary sequences, which can be formed during polymerization of the index from nucleotide or oligonucleotide sub-units. Then linkages may be performed enzymatically, for example, with a polymerizing enzyme, ligation enzyme, transposase, or other enzyme that may form bonds.

3D localization of the immobilization chemistry may be achieved via 3D spatial gating of the immobilization chemistry. 3D spatial gating may be achieved either by 3D in situ site-directed methods, in serial or in parallel, or by the accumulation of patterned 2D layers to achieve a 3D pattern, in a manner analogous to stereolithography. 2D and 3D light patterns may be generated using a number of approaches, such as, for example, photolithography. Spatial light patterning techniques can include scanning and parallel techniques, wherein according to scanning approaches one or more small spots of light are displaced to the targeted regions, such as by using galvanometric mirrors or acousto-optic deflectors, and according to parallel techniques the light beam can be spatially shaped to simultaneously cover all targeted regions by modulating either the light intensity or the phase of the illumination beam in space. With amplitude modulation, light patterns can be created by selectively blocking light rays that illuminate regions of no interest, while with phase modulation, the wavefront of the light beam can be locally modified so that light rays can be directed onto the target.

In some embodiments, interference patterns are used, including interference patterns with patterns of greater resolution than the diffraction limit. In some embodiments, one or more scanning light sources are used, either as single-photon or multi-photon excitation systems, wherein the former can use a single photon of a certain wavelength of light to trigger a chemical change, and the latter technique, also known as non-linear and two-photon excitation, can utilize the simultaneous absorption of two photons in a single quantitated event to trigger a chemical change. In some embodiments, one or more pinholes, such as a pinhole array, may be used to localize light within the volume. In some embodiments, one or more digital spatial light modulator (SLM) may be used, including those based on one of the three known digital projection technologies, transmissive liquid crystal, reflective liquid crystal on silicon (LCOS), digital light processing (DLP: moving micro mirror), or digital micromirror device (DMD). In some embodiments, three-dimensional holographic photopatterning techniques may be used, such as by using the Gerchberg-Saxton algorithm and an electrically addressed spatial light modulator (SLM) to create and display phase holograms, respectively, enabling arbitrary and efficient parallel photo-patterning. Various other 3D holographic photopatterning techniques may be used. In some embodiments, remote focusing approaches may be used for higher-speed axial spatial light modulation. In some embodiments, adaptive optics may be used to correct for wavefront errors, such as those induced by changes in refractive index, improving the precision of spatial light patterning.

According to one aspect, the accumulation of the 3D index pattern, either by sub-volume or layer deposition, is coincident with matrix construction, wherein the immobilization linkage is by co-polymerization of index or index subunits comprising an acryloyl moiety, or separately wherein the immobilization linkage can be formed subsequent to matrix construction within the sub-volume or layer, such that the linkage sites can be either fully consumed or excess sites can be subsequently rendered inoperative, thereby localizing the linkage to the newly formed sub-volume or layer. According to one embodiment of this aspect, formation of the matrix can comprise a photopolymerization step, such as by photopolymerization of polyacrylamide. According to a separate aspect, accumulation of the 3D index pattern can be subsequent to formation of the 3D matrix.

Photoactivated immobilization chemistry, either by patterning of en block index molecules or in situ synthesis, can be mediated by variety of light-directed chemistries. Photoactivated immobilization chemistry can be used to immobilize an index or a plurality of indices in the 3D matrix. Photoactivation may be achieved by a number of chemical approaches related to photochemistry, including by removal of photolabile protecting groups, such as nitroveratryloxy carbonyl (NVOC), 2-nitrobenzyl-, 6-nitropiperonyl, or 9-anthrylmethyl groups, or by the use of compounds which undergo conformational changes upon light exposure, such as cyclic azobenzene derivatives, which can undergo cis-trans isomerization when exposed to visible light, triggering conformational changes, such as those that induce or block base-pairing or formation, or triggering a local chemical change. According to one aspect, a photo-modulated chemistry can be used wherein a catalyst is deprotected or activated or light triggers a change in the local chemical environment. One such example can include the use of photogenerated acid (PGA) trigger, which may be used for deprotection of the 5'-OH group in conventional nucleotide phosphoramidite monomers (i.e. PGA-gated deprotection). Light may be used to control a click reaction. DNA adducts of 1-(4,5-dimethoxy-2-nitrophenyl)ethyl ester (DMNPE) may modulate DNA hybridization and polymerase activity, including RNA polymerases for in vitro transcription. Thermal reactivity can be modulated using a light-controlled manifold, for example by photodeactivation of triazolinediones (TADs) under visible light irradiation enabling a UV light-switchable reaction selectivity between a photoenol and thermal TAD-based reaction. Photosensitive nucleic acid binders (NABs) may be used to modulate DNA conformation in a sequence-independent manner.

According to one aspect, using en bloc index molecules, the indexing biochemistry can comprise the spatial immobilization chemistry, i.e., spatial localization of the index molecule can be coincident with some aspect of the indexing biochemistry, such as by the activity of a nucleic acid ligase, nucleic acid polymerase, by nucleic acid hybridization, or by other indexing reaction mechanisms described herein.

3D Spatial Indexing by In Situ Sequencing

According to embodiments of the present disclosure using an SMI field wherein the pattern of index sequences may not be predetermined, as by in situ field synthesis, described herein, the spatial pattern can be determined by in situ sequencing.

The in situ sequencing read, comprising the SMI, may be generated using various in situ sequencing approaches, including, but not limited to, SBH, SBS, or SBL. Any sequence of fluorescent signals generated in situ (the totality of which are considered the "sequencing read"), which can correspond to a linear sequence of nucleobase identities present on the template molecule, but in the general case may constitute any temporally ordered set of fluorescent signals generated by the template through FISSEQ serving the purpose of conveying information about the sequence of the template, may function as the SMI. Therefore the SMI as detected in situ may not comprise a linear sequence of nucleotides present on the template. Rather, any information comprising a sequencing read, in the broad sense, may be used for the purpose of identification or inference of the spatial origin of a corresponding in vitro sequencing read.

As described herein, the spatial index pattern may be determined prior to, or subsequent to, other steps of the assay, including the indexing reaction and isolation of indexed material for in vitro assay.

According to certain embodiments of the present disclosure, sequences present in a FISSEQ library can be used directly or indirectly as the SMI for target molecules other than the original molecular templates of the FISSEQ library, wherein the FISSEQ library comprises an RNA or DNA FISSEQ library.

In accordance with certain examples, methods of sequencing nucleic acid in situ within a matrix are provided. General sequencing methods, such as sequencing by extension with reversible terminators, fluorescent in situ sequencing (FISSEQ), pyrosequencing, massively parallel signature sequencing (MPSS) and the like, can be used with the matrix in which the nucleic acids are present. Reversible termination methods use step-wise sequencing-by-synthesis biochemistry that coupled with reversible termination and removable fluorescence. FISSEQ is a method whereby DNA can be extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles can be bleached or digitally subtracted or the fluorophore can be cleaved from the nucleotide and washed away. Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction can be detected by ATP sulfurylase and luciferase in a coupled reaction which can be visibly detected. The added nucleotides can be continuously degraded by a nucleotide-degrading enzyme. After the first added nucleotide has been degraded, the next nucleotide can be added. As this procedure is repeated, longer stretches of the template sequence can be deduced. MPSS utilizes ligation-based DNA sequencing simultaneously on microbeads. A mixture of labelled adaptors comprising all possible overhangs is annealed to a target sequence of four nucleotides. The label can be detected upon successful ligation of an adaptor. A restriction enzyme is then used to cleave the DNA template to expose the next four bases.

Indexing Reactions

The spatial molecular index (SMI) can be conferred upon target molecules for detection via a chemical linkage, such as those formed by nucleic-acid reactions, referred to herein as indexing reactions. The linkage between the spatial index and the target molecule may need to be robust to the assay conditions, such that the linkage can be maintained throughout the assay, thereby enabling localization. The linkage may be formed in parts, wherein at least some aspect of the linkage is formed in situ. The final product of the indexing reaction can comprise a template for nucleic acid assay, such as by next-generation sequencing, comprising both the SMI sequence(s) and template sequence(s). The in situ library can comprise a plurality of the templates. The SMI can be linked or coupled to the 3D matrix before the linkage with the target molecule. The SMI can be linked or coupled to the 3D matrix after the linkage with the target molecule. The SMI can be linked or coupled to the 3D matrix at the same time as the linkage with the target molecule occurs. The target molecule can also be linked or coupled to the 3D matrix and the SMI can be subsequently attached. The target molecule can also be linked or coupled to the 3D matrix after or during attachment to the SMI.

Suitable nucleic acid linkages include, but are not limited to, the phosphodiester bonds formed within the backbone of a nucleic acid strand, and hydrogen bonds formed by the base-pairing of complementary sequences. Other non-nucleic acid linkages include those formed by click reactions or chemical conjugations, such as bioconjugation reactions. According to some aspects using the latter non-nucleic acid linkages, the persistent proximity of the spatial index and target sequences may enable proximity-dependent nucleic acid reactions, such as proximity ligation and template switching, which can confer the SMI sequence(s) into the template.

According to certain embodiments, the target molecule can act as a template for a nucleic acid polymerization reaction, and/or as a primer for a nucleic acid polymerization reaction. According to certain embodiments, the spatial indexing molecule can act as a template for a nucleic acid polymerization reaction, and/or as a primer for a nucleic acid polymerization reaction. According to certain embodiments, a template switching polymerization reaction can be used, whereby two molecules, of the set of molecules comprising a target molecule and spatial indexing molecule, both can serve as a template for a nucleic acid polymerization reaction.

According to certain embodiments, a nucleic acid ligation reaction can be used, including, but not limited to the reactions of, splint ligation, single-stranded DNA or RNA ligation, blunt-end ligation, cohesive-end ligation, hybrid DNA-RNA ligation, DNA-DNA ligation, RNA-RNA ligation, and circularization.

Target molecules can include any molecule which may be spatially indexed for the purpose of identifying the spatial origin of the target molecule during in vitro assay. The target molecules may be RNA or cDNA, or a subset of molecular species thereof. The target molecules may be DNA. The target molecules may be endogenous nucleic acid molecules that are in the sample. The target molecules may for example be mRNA and identifying the spatial origin may indicate the location of expression of a particular protein. The target molecules may be synthetic nucleic acid molecules. The target molecules may be barcodes or any sequence suitable for molecular identification or inference, such as those used to label antibodies and other affinity binding molecules, such as aptamers, or nucleic acid probes, such as in situ hybridization probes. Multiple species of target molecules may be indexed together, using a single spatial index field, simultaneously or in series. Alternatively, the spatial indexing reactions may be partitioned, or indexed, by one or more criteria, including molecular species and type of biomolecule. According to one embodiment, the indexing reaction can be multiomic, encompassing species which are members of two or more "omes", including, but not limited to, the genome, transcriptome, and proteome.

According to certain embodiments, one or more sequences can be used, as a part of the spatial indexing molecule or spatial indexing reaction, such as a primer or splint oligonucleotide, to direct the spatial indexing reaction in a sequence-dependent manner. Further according to one such embodiment, a poly(dT) sequence can be used to direct the indexing reaction to polyadenylated RNA.

SMI and Template Detection by In Vitro Sequencing

To practice the present disclosure, the in situ library can be captured, physically or informationally, and sequenced in vitro. According to some embodiments, the in situ library can be subjected to FISSEQ for the purpose of detecting the SMI, and subsequently the nucleic acids can be collected from the in situ library and used directly or indirectly as the input to an in vitro sequencing assay. According to some other embodiments, nucleic acid molecules derived from the in situ sequencing library, during or subsequent to library construction, can be collected, and used directly or indirectly as the input to an in vitro sequencing assay.

The in situ library can be used as the input for in vitro sequencing library construction, including but not limited to the steps of nucleic acid isolation or purification, fragmentation, adapter ligation, polymerase chain reaction, etc., or used directly in an in vitro sequencing assay, such as by nanopore sequencing.

According to some embodiments, the nucleic acid material comprising the in situ library may be collected by separating or purifying the nucleic acid material from the 3D matrix. In the case the nucleic acid material is chemically linked to the 3D matrix, the 3D matrix may be chemically degraded, dissolved, or otherwise made to release the nucleic acid material. For example, the nucleic acid material may be linked to the 3D matrix via cleavable linkers and the nucleic acid material can be released from the 3D matrix by cleaving the linkers. The cleavable linkers can be chemically cleavable linkers or photo-cleavable linkers. In the case where the 3D matrix is substantially a polyacrylamide matrix, the nucleic acid material may be collected as described in US 2018/0119219. For example, the polyacrylamide matrix can be formed by polyacrylamide-bisacrylamide (PA-BIS) copolymer with N,N'-Bis(acryloyl)cystamine (BAC) cross-linkers, and in such case, the polyacrylamide matrix can be disrupted upon electrochemical induction by reduction of the disulfide, breaking at least a subset of cross-links within the matrix. Nucleic acid material can then be released from the disrupted polyacrylamide matrix. Methods of dissolving the 3D matrix can be dependent on the chemical composition of the 3D matrix, but can include mechanisms for chemically breaking linkages within the 3D matrix, such as bonds within the polymer backbone or cross-links. According to one embodiment, a protease reaction can be used. Alternatively, the chemical bonds linking the nucleic acids to the 3D matrix may be selectively broken. Methods of nucleic acid purification include precipitation, purification by size, affinity pull-down, electrophoretic focusing, and other methods. The purification by size can comprise using silica columns or beads, for example, in combination with chaotropic salts and/or under certain pH conditions. The affinity pull-down can comprise using beads or surfaces coated with DNA or biotin to capture nucleic acids.

According to some embodiments, nucleic acid molecules can be derived from the in situ library. Isolation of the derivative molecules from the in situ library may be enabled by the physical linkages formed between the nucleic acid molecules comprising in situ library, or precursors thereof, and the 3D matrix, Derivative molecules may be formed by various mechanisms, including but not limited to synthesis of one or more nucleic acid molecules complementary to the sequencing template, such as by nucleic acid polymerization including DNA PCR, RCA, hyperbranch RCA, and RNA in vitro transcription (IVT). In some cases, derivative molecules can be generated by amplification of the sequencing templates; in the case isolation and the subsequent in vitro sequencing assay can have less than 100% per-molecule sensitivity, amplification during sequencing may prevent or reduce the loss of sequencing templates within the pool of derivative sequences. Example embodiments can include using the in situ library templates, or precursor molecules thereof, as solid-state templates of second strand synthesis, PCR, IVT, RCA, or hyperbranch amplification, and subsequently collecting the derivative nucleic acid molecules using the methods described herein.

Further, according to this embodiment, nucleic acid molecules can be separated from the FISSEQ matrix using methods including, but not limited to, melting a nucleic acid duplex, diffusing nucleic acids out of the 3D matrix, and/or electrophoretically pulling nucleic acids out of the 3D matrix. Furthermore, the nucleic acid molecules may be subsequently purified and concentrated using methods including, but not limited to, bead pull-down, nucleic acid precipitation, and electrophoretic focusing.

Such nucleic acid material may be readily assayed using methods for in vitro nucleic acid sequencing.

Various methods can be used for nucleic acid sequencing, including, but not limited to Sanger sequencing, next generation sequencing, quantitative polymerase chain reaction (PCR), multiplexed PCR, DNA sequencing, RNA sequencing, and de novo sequencing. Sequencing may include sequencing by synthesis, sequencing by ligation, and sequencing by hybridization. Sequencing may include massively parallel array sequencing (e.g., Illumina), whole genome sequencing, and deep sequencing. Sequencing may include single molecule sequencing (e.g., Pacific Biosciences of California and Oxford Nanopore). Sequencing may include massively parallel signature sequencing (MPSS), polony sequencing, and pyrosequencing. Sequencing may include nanopore sequencing (e.g., Oxford Nanopore, Genia and Quantum Biosystems), sequencing with mass spectrometry, microfluidic Sanger sequencing, microscopy-based sequencing techniques, RNA polymerase (RNAP) sequencing, and fluorescence hybridization-based technology (e.g., but not limited to nanoString nCounter(hybridization technology). Sequencing may include the use of one or more sequencing modalities.

Furthermore, one or more in vitro sequencing reads may be generated using any sequencing methods, including, but not limited to, sequencing by synthesis, sequencing by ligation, sequencing by hybridization, nanopore sequencing, and pyrosequencing. In some cases, the sequencing method may include next generation sequencing. Various platforms can be used for the next generation sequencing, for example, Illumina, Roche 454, Life SOLID, Life Ion Torrent, Pacific Biosciences, and Oxford Nanopore. In some cases, the sequencing method may include array-based sequencing, such as, for example. Polony FISSEQ. Polony FISSEQ can comprise amplifying (e.g., using PCR amplification) of a library of linear nucleic acid molecules in a gel matrix (e.g., polyacrylamide gel) on a support to generate a library of polymerase colonies or polonies, and sequencing the polonies.

In some cases, a sequencing platform which can produce long sequencing reads (e.g., greater than or equal to about 10,000, 20,000, 50,000, 100,000, 200,000, 500,000, 1,000,000 or more bases per read) may be used. In particular, sequencing by synthesis, pyrosequencing, single molecule real-time sequencing, nanopore sequencing, ion semiconductor sequencing, and other sequencing platforms and methods can produce reads longer than reads generated by in situ sequencing. For example, in nanopore sequencing, a strand of nucleic acid can be passed through a nanopore. The current can be changed as the bases G. A. T/U and C pass through the pore in different combinations. For another example, ion semiconductor sequencing (e.g., Ion Torrent) is a method of DNA sequencing based on the detection of hydrogen ions that can be released during the polymerization of DNA. This method is also a "sequencing by synthesis" method during which a complementary strand can be built based on the sequence of a template strand.

The in vitro sequencing chemistries that utilize fluorescence imaging can be used. For example, sequencing method utilizing sequencing by ligation and fluorescence imaging include ABI SOLID (Life Technologies), in which a sequencing primer on a template can be ligated to a library of fluorescently labeled nonamers with a cleavable terminator. After ligation, the beads can then be imaged using four color channels (e.g., FITC, Cy3, Texas Red and Cy5). The terminator can then be cleaved off leaving a free-end to engage in the next ligation-extension cycle. After all dinucleotide combinations have been determined, the images can be mapped to the color code space to determine the specific base calls per template. The workflow can be achieved using an automated fluidics and imaging device (e.g., SoLiD 5500 W Genome Analyzer. ABI Life Technologies). Another example sequencing platform uses sequencing by synthesis, in which a pool of single nucleotide with a cleavable terminator is incorporated using DNA polymerase. After imaging, the terminator can be cleaved and the cycle can be repeated. The fluorescence images can then be analyzed to call bases for each DNA amplicons within the flow cell (e.g., HiSeq, Illumina).

SMI and Template Detection by Using Probe Molecules

The sequences of spatial indices may also be determined by detection or use of probe molecules. Probe molecules may be nucleic acid molecules. The probes may be padlock probes, molecular inversion probes, molecular beacon probes, reverse transpiration primers, second strand synthesis primers or other primers used for nucleic acid amplification described herein. The probes may preferentially bind a sequence over another sequence. The probes may emit a signal when hybridized to a sequence to allow identification of the sequence and/or the identification of a particular location. The probes may be used to synthesize or amplify nucleic acids which may be subjected to sequencing reactions as described herein.

The probes may be ribonucleic acid, deoxyribonucleic acid, or other derivatives, or any combinations thereof. The probes may be of a particular length. For example, the probes may be less than or equal to 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, or 2 nucleotides long. For example, the probes may be greater than or equal to 2, 3, 4, 5, 6, 7, 8, 9, 10, 11, 12, 13, 14, 15, 16, 17, 18, 19, 20, 25, 30, 35, 40, 50, or more nucleotides long. The probes may be of any configurations, including but not limited to linear, circular, and stem-loop.

In some cases, the probe molecules may be protein molecules. For example, the probe molecules may be antibodies, fragments of antibodies, or derivatives of antibodies. The probe molecules may be nucleic acid binding proteins. The nucleic acid binding proteins may bind preferentially to specific sequences. The nucleic acid binding proteins may bind non-specifically. The nucleic acid proteins may bind a specific nucleotide or nucleotide derivate, or may bind a particular structure of nucleic acid.

Methods of Analysis and Data Integration

A 3D spatial map of SMI sequences can be constructed and/or stored, such as by using a computer, using the methods described herein. SMI sequences can be identified in one or more sequencing datasets, such as by computational processing of sequencing read datasets, including, but not limited to, using the methods of string parsing using a pointer or reference sequence. Methods for matching SMIs among these two or more datasets can include methods of sequence comparison, such as by string lookup, or other bioinformatics methods, such as by using local alignment or short read alignment methods, which can enable inference of corresponding SMI sequences despite errors.

Analysis of the sequences may include identifying one or more genetic aberrations in the plurality of nucleic acid molecules sequenced. A genetic aberration may be a copy number variation, a single nucleotide variation, an insertion or a deletion. In some cases, two or more nucleic acid molecules which are identified as having one or more genetic aberration may comprise the same index sequence. Identifying one or more genetic aberrations and correlating the one or more genetic aberrations with a spatial index may, for example, allow identification of the expression and location of a particular genetic aberration.

In some cases, the analysis may use databases and computer processing to aid in analysis. For example, the analysis may use a database that comprises 3D spatial data indicative of a 3D spatial position of nucleic acid molecules in a synthetic 3D matrix. The database may store sequencing data comprising sequences of nucleic acid molecules or derivatives of the nucleic acids. The database may store a subset of the data such that a subset of spatial data and/or sequences is stored. The database may be accessed by a computer processor to retrieve the 3D spatial data and associate the sequences of the nucleic acid with the 3D spatial position and 3D spatial origin of the molecule in the cell or cell derivative.

Computer Systems

Figure 3:
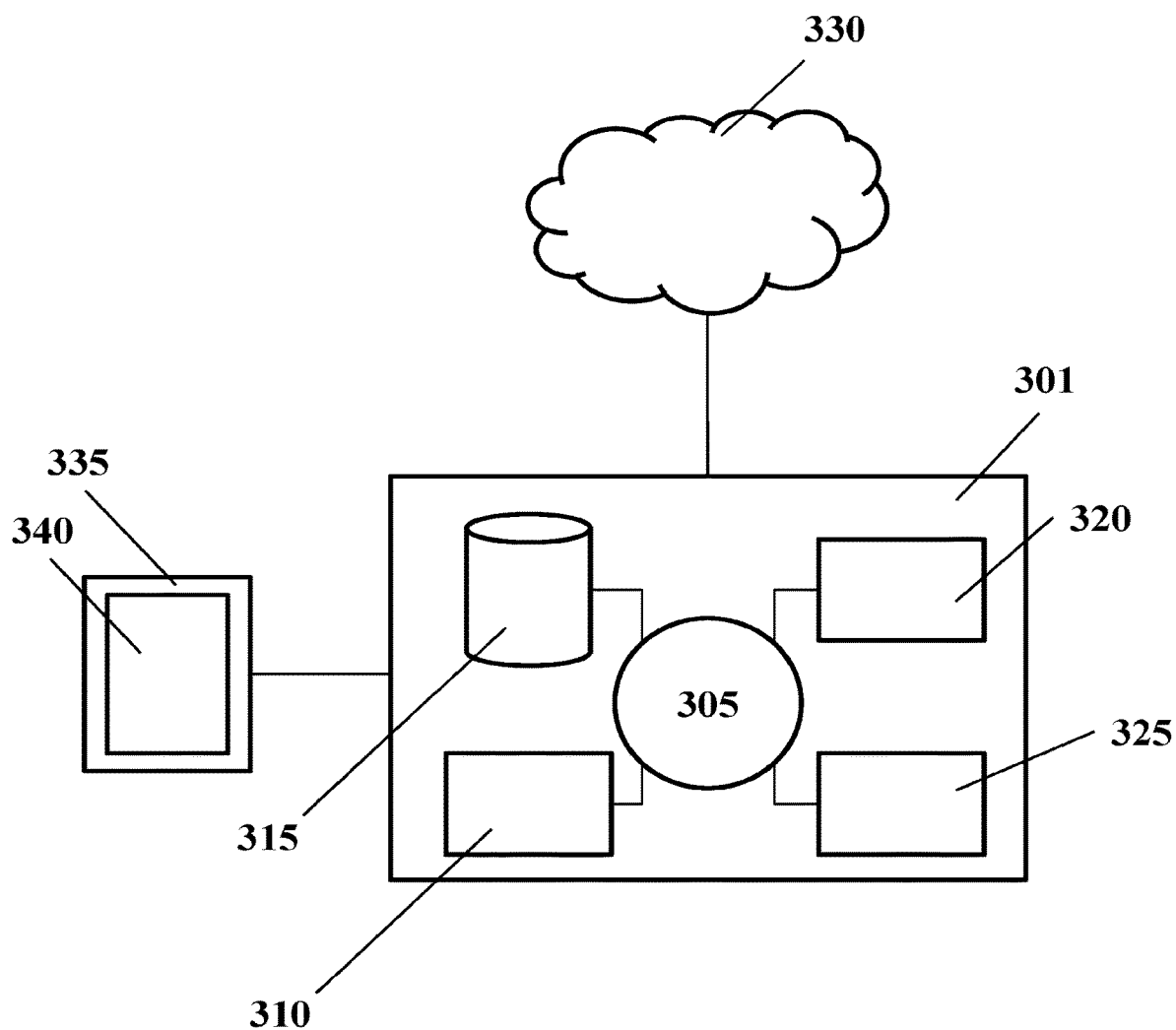
FIG. 3 shows a computer system that is programmed or otherwise configured to implement methods provided herein.

The present disclosure provides computer systems that are programmed to implement methods of the disclosure. FIG. 3 shows a computer system 301 that is programmed or otherwise configured to aid in generating libraries of indices, processing sequencing reads, or sequencing nucleic acids (in situ and in vitro). The computer system 301 can regulate various aspects of the present disclosure, such as, for example, store data relating to 3D spatial positions of nucleic acids, compare sequences obtained from the in situ and in vitro sequencing reads, align sequencing reads, map spatial indices, generate outputs regarding spatial positions. In some aspects, the computer system may be programmed to control release of reagents, activation of reactions (e.g., amplification reactions), and/or may initiate a sequencing reaction to take place. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user (e.g., a user generating the indices of the current disclosure or a user utilizing such indices). Examples of remote computer systems include personal computers (e.g., portable PC), slate or tablet PC's (e.g., Apple® iPad, Samsung® Galaxy Tab), telephones. Smart phones (e.g., Apple® iphone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables: copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, the spatial origin of nucleic acid molecules, showing detection and/or sequencing of biomolecules of interest, or generating or displaying an electronic report associating the 3D spatial position with a sequence of ta nucleic acid molecule. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, be executed to generate the indices of the current disclosure, or map and align sequencing reads to identify a spatial origin of a given sequence.

EXAMPLES

Example 1: Analysis of a Standard FISSEQ Library

A biological sample will be fixed using a fixative or embedded in a hydrogel. A FISSEQ library will be constructed using by the use of reverse transcriptase of RNA to generate cDNA. The library can be sequenced in situ using standard FISSEQ techniques. The matrix will be dissolved using enzymatic or chemical reactions to break linkages in the matrix. In this example, the proteinase K will be used to dissolve the gel and the DNA extraction will be performed via a phenol chloroform extraction and/or DNA purification columns. For hydrogel embedded matrices, sodium periodate may be used to digest acrylate gels containing DHEBA crosslinker without damaging nucleic acids. The nucleic acids will be processed for in vitro sequencing by methods, such as appending adapters for use in high throughput sequencing. The sequences of generated by the longer reads of the in vitro sequencer can be correlated and matched using a computer processor to the sequencing reads of the in situ reads to determine the spatial location of the longer read.

Example 2: Analysis Using a Barcoded FISSEQ Library

A biological sample will be fixed using a fixative or embedded in hydrogel. The nucleic acids in the biological sample will be primed using a primer comprising an exogenous SMI. The primer may comprise a oligo(dT) portion as well as the SMI to allow priming to mRNA along with the incorporation of the SMI. In situ sequencing will then be performed using standard FISSEQ techniques such as sequencing by ligation or sequencing by synthesis. The matrix will then be dissolved using enzymatic or chemical reactions to break linkages in the matrix. In this example, the proteinase K will be used to dissolve the gel and the DNA extraction will be performed via a phenol chloroform extraction and/or DNA purification columns. For hydrogel embedded matrices, sodium periodate may be used to digest acrylate gels containing DHEBA crosslinker without damaging nucleic acids. The nucleic acids will be processed for in vitro sequencing by methods such as appending adapters for use in high throughput sequencing. The sequences generated by the longer reads of the in vitro sequencing can be correlated using the SMI sequence. This SMI sequence is then matched to the location of the SMI sequence of the in situ reads to determine the spatial location of the longer read.

Example 3: Capture by Probe Circularization

A biological sample will be fixed or otherwise embedded in a hydrogel. The nucleic acids in the biological sample will be hybridized with a probe or a plurality of probes comprising a SMI sequence. The probe will be constructed such that it can be circularized, for example a molecular inversion probe or padlock probe. The probe may hybridize preferentially to a particular gene, or mutation of a gene such as a single nucleotide polymorphism (SNP), an insertion, a deletion, or a combination thereof. The hybridized sequence may be ligated or subjected to an extension reaction to circularize the nucleic acid molecule. Following circularization, the nucleic acid molecule can be subjected to RCA to amplify the amount of nucleic acid and increase the signal. In situ sequencing can be performed on the capture nucleic acid molecule to identify the SMI sequence. The matrix will be dissolved using enzymatic or chemical reactions to break linkages in the matrix. In this example, the proteinase K will be used to dissolve the gel and the DNA extraction will be performed via a phenol chloroform extraction and/or DNA purification columns. For hydrogel embedded matrices, sodium periodate may be used to digest acrylate gels containing DHEBA crosslinker without damaging nucleic acids. The nucleic acids may be processed for in vitro sequencing by various approaches, such as by appending adapters for use in high throughput sequencing. In vitro sequencing of the nucleic acid will be performed and sequencing reads can be generated corresponding to the SMI and the nucleic acid. The sequences generated by the longer reads of the in vitro sequencing can be correlated using the SMI sequence. This SMI sequence will then be matched to the location of the SMI sequence of the in situ reads to determine the spatial location of the longer read.

Example 4: Rolony Second-Stranding and Isolation

A biological sample will be fixed or otherwise embedded in a hydrogel. An SMI sequence will be attached to the nucleic acids. SMI may be attached using ligation, extension, or transposition. The SMI and corresponding attached nucleic acid will be subjected to rolling circle amplification to generate a rolony. A reverse primer and DNA polymerase will be used to generate DNA complementary to the rolony. The new generated complementary DNA (second strand DNA) will be collected, isolated, and processed for in vitro sequencing. The rolony library will be subjected to in situ sequencing, such as FISSEQ, to generate short reads of the SMI. The second strands will be sequenced using in vitro sequencing technology. The in vitro sequencing data and the in situ sequenced data will be integrated and matched via a computer processor to determine the complete sequence and location based on the SMI.

Alternatively, a biological sample will be fixed or otherwise embedded in a hydrogel. An SMI sequence will be attached to the nucleic acids. SMI may be attached using a method describes elsewhere, for example ligation, extension, circularization, or transposition. The SMI and corresponding attached nucleic acid will be subjected to rolling circle amplification to generate a rolony. A primer and RNA polymerase will be used to generate RNA complementary to the rolony. The new generated RNA will be collected, isolated, and processed for in vitro sequencing. The rolony library will be subjected to in situ sequencing to generate short reads of the SMI. The second strands will be sequenced using in vitro sequencing technology. The in vitro sequencing data and the in situ sequenced data will be integrated and matched via a computer processor to determine the complete sequence and location based on the SMI.

Example 5: Polony/Rolony SMI Field Indexing

A biological sample will be fixed or otherwise embedded in a hydrogel as to form a 3D matrix. An array of polonies or rolonies amplicons comprising a random sequence domain will be generated throughout the 3D matrix. The nucleic acid molecules native to the sample will be indexed by attaching a random sequence domain index to the nucleic acid molecules. The indexed nucleic acids will then be collected and processed for sequencing. In vitro sequencing using a next generation sequencer will be performed to obtain the sequence of the native nucleic acid and the index. In situ sequencing by FISSEQ will be performed on the polonies or rolonies to map the spatial index sequences. Using computer processing sequencing reads of the indexed nucleic acids can be correlated to the FISSEQ reads of the spatial index sequences and thus mapped to a particular spatial location.

Figure 4A:
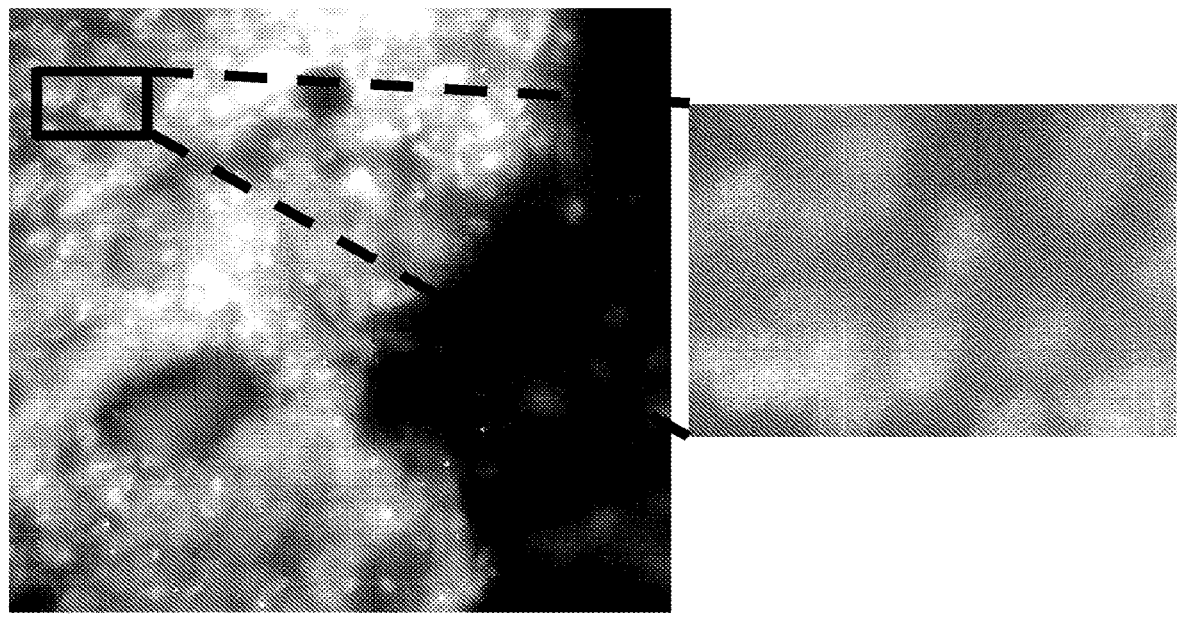
FIG. 4A shows an example image of a tissue sample. Tissue autofluorescence and nuclei are shown.
Figure 4B:
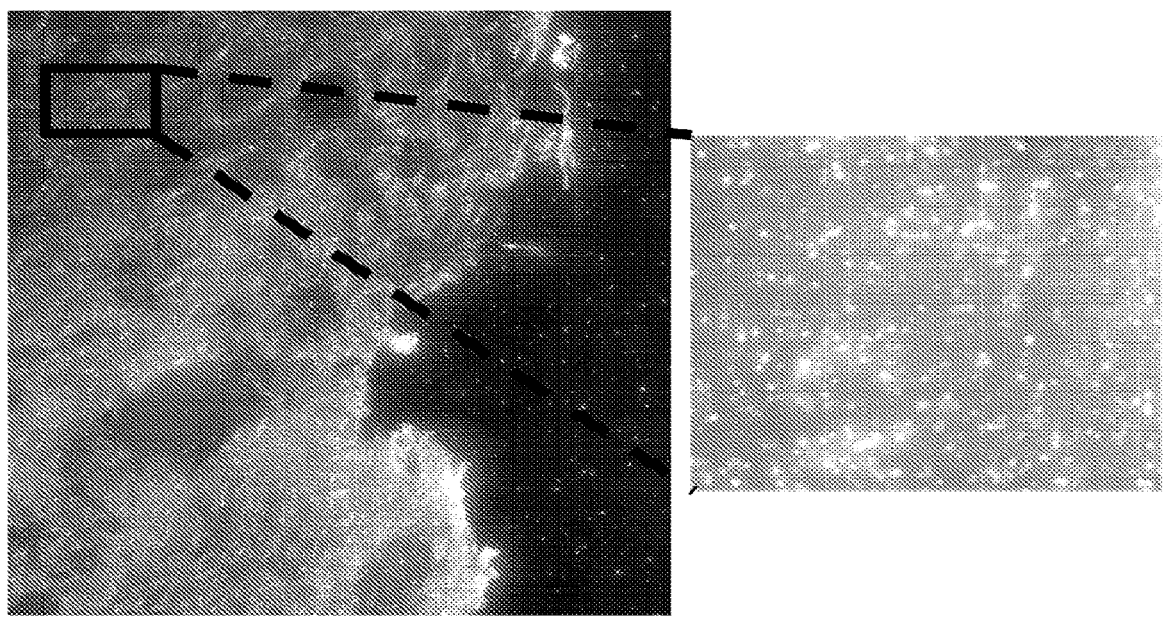
FIG. 4B shows an example image of synthetic indexing rolonies generated in the tissue sample. The synthetic indexing rolonies are labeled with fluorescent primer hybridized to a common sequence domain.

FIG. 4A and FIG. 4B show an example tissue sample and synthetic indexing rolonies generated in the tissue sample. FIG. 4A shows an image of the tissue sample embedded within a 3D matrix. The tissue was fixed using a fixation agent described herein and embedded within the 3D matrix. Reverse transcription primers were used to generate complementary DNA (cDNA) molecules of target mRNA molecules within the tissue sample. Probes were used to hybridize with the cDNA molecules. Each probe comprised an indexing sequence and a common sequence. The common sequence was the same between different probes. The probes were circularized and amplified to generate rolonies (e.g., synthetic indexing rolonies). The common sequence of the probes can be used to hybridize with detection probes or sequencing primers for further analysis. FIG. 4B shows synthetic indexing rolonies labeled with fluorescent primer hybridized to the common sequence. Several aspects are described with reference to example applications for illustration. Unless otherwise indicated, any embodiment may be combined with any other embodiment. It should be understood that numerous specific details, relationships, and methods are set forth to provide a full understanding of the features described herein. A skilled artisan, however, will readily recognize that the features described herein may be practiced without one or more of the specific details or with other methods. The features described herein are not limited by the illustrated ordering of acts or events, as some acts may occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, or within 2-fold, of a value. Where particular values are described in the application and claims, unless otherwise stated the term "about" meaning within an acceptable error range for the particular value may be assumed.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing or analyzing a nucleic acid molecule having a three-dimensional (3D) spatial position in a cell or cell derivative, comprising:
    (a) using a transposase to insert a nucleic acid index sequence into said nucleic acid molecule to generate an indexed nucleic acid molecule comprising said nucleic acid index sequence;
    (b) detecting said nucleic acid index sequence of said indexed nucleic acid molecule to identify said 3D spatial position;
    (c) subsequent to (b), removing said indexed nucleic acid molecule or derivative thereof from said 3D spatial position; and
    (d) identifying a sequence of said indexed nucleic acid molecule or derivative thereof removed from said 3D spatial position in (c).

2. The method of claim 1, wherein said sequence identified in (d) identifies said 3D spatial position identified in (b).

3. The method of claim 1, wherein (d) comprises sequencing said indexed nucleic acid molecule or derivative thereof removed from said 3D spatial position in (c).

4. The method of claim 1, wherein said sequence of said indexed nucleic acid molecule or derivative thereof comprises said nucleic acid index sequence.

5. The method of claim 1, wherein said nucleic acid molecule is a ribonucleic acid (RNA) molecule.

6. The method of claim 1, wherein said nucleic acid molecule is a deoxyribonucleic acid (DNA) molecule.

7. The method of claim 1, further comprising contacting said cell or cell derivative with a probe molecule.

8. The method of claim 7, further comprising, prior to (c), generating an amplification product using said probe molecule and said indexed nucleic acid molecule, wherein said amplification product comprises said nucleic acid index sequence.

9. The method of claim 8, further comprising performing rolling circle amplification (RCA) or polymerase chain reaction (PCR) to generate said amplification product.

10. The method of claim 8, wherein said cell or cell derivative is embedded in a synthetic 3D matrix and said amplification product is attached to said synthetic 3D matrix.

11. The method of claim 1, wherein said cell or cell derivative is embedded in a synthetic 3D matrix.

12. The method of claim 11, wherein said nucleic acid molecule is attached to said synthetic 3D matrix.

13. The method of claim 12, wherein said indexed nucleic acid molecule or derivative thereof is attached to said synthetic 3D matrix.

14. The method of claim 13, wherein said indexed nucleic acid molecule or derivative thereof is reversibly attached to said synthetic 3D matrix.

15. The method of claim 14, wherein (c) comprises releasing said indexed nucleic acid molecule or derivative thereof from said synthetic 3D matrix.

16. The method of claim 11, wherein said synthetic 3D matrix cannot expand.

17. The method of claim 1, wherein said cell or cell derivative is fixed.

18. The method of claim 17, wherein said cell or cell derivative is formaldehyde-fixed or glutaraldehyde-fixed.

19. The method of claim 1, wherein said nucleic acid index sequence comprises a unique molecular index (UMI).

20. The method of claim 1, wherein said indexed nucleic acid molecule generated in (a) comprises an adaptor sequence.

* * * * *